(12) United States Patent
Nobles et al.

(10) Patent No.: US 11,642,181 B2
(45) Date of Patent: May 9, 2023

(54) USER ARM SUPPORT FOR USE IN A ROBOTIC SURGICAL SYSTEM

(71) Applicant: Verb Surgical Inc., Santa Clara, CA (US)

(72) Inventors: Brent Michael Nobles, Palo Alto, CA (US); Joan Savall, Palo Alto, CA (US)

(73) Assignee: Verb Surgical Inc., Sam Clara, CA (US)

(*) Notice: Subject to any disclaimer, the term of this patent is extended or adjusted under 35 U.S.C. 154(b) by 597 days.

(21) Appl. No.: 16/732,833

(22) Filed: Jan. 2, 2020

(65) Prior Publication Data

US 2020/0214773 A1 Jul. 9, 2020

Related U.S. Application Data

(62) Division of application No. 15/624,579, filed on Jun. 15, 2017, now Pat. No. 10,568,703.

(Continued)

(51) Int. Cl.
*A61B 34/30* (2016.01)
*B25J 13/08* (2006.01)
(Continued)

(52) U.S. Cl.
CPC ............. *A61B 34/25* (2016.02); *A47B 21/02* (2013.01); *A47B 21/03* (2013.01); *A47B 21/04* (2013.01);
(Continued)

(58) Field of Classification Search
CPC ... A61B 34/25; A61B 17/00234; A61B 34/30; A61B 34/74; A61B 90/60;
(Continued)

(56) References Cited

U.S. PATENT DOCUMENTS 5,254,066 A * 10/1993 Brown ............... A63B 24/0062
601/40
8,120,301 B2 * 2/2012 Goldberg ............... G16H 40/67
318/432

(Continued)

FOREIGN PATENT DOCUMENTS

| CN | 105283144 | 1/2016 |
| CN | 105395295 A | 3/2016 |

(Continued)

OTHER PUBLICATIONS

Non-Final Office Action for U.S. Appl. No. 16/745,090 dated Dec. 27, 2021, 8 pages.

(Continued)

*Primary Examiner* — Jaime Figueroa
(74) *Attorney, Agent, or Firm* — Aikin & Gallant, LLP

(57) ABSTRACT

A user system for a robotic surgical system, the user system including a handheld groundless user interface device configured to control the robotic surgical system, and a user console. The user console includes a seat and a first adjustable, ergonomic arm support linkage coupled to the seat, in which the first arm support linkage is movable between a folded storage configuration and at least one unfolded use configuration corresponding to at least one of a user characteristic and a surgical task characteristic. The at least one unfolded use configuration may be pre-stored in a database.

10 Claims, 17 Drawing Sheets

Related U.S. Application Data

(60) Provisional application No. 62/397,823, filed on Sep. 21, 2016.

(51) Int. Cl.
  B25J 13/06      (2006.01)
  A61B 34/00      (2016.01)
  A61B 90/60      (2016.01)
  B25J 13/02      (2006.01)
  A47C 1/00       (2006.01)
  A61B 17/00      (2006.01)
  B25J 9/16       (2006.01)
  A47B 21/02      (2006.01)
  A47B 21/03      (2006.01)
  A47B 21/04      (2006.01)

(52) U.S. Cl.
  CPC .......... *A47C 1/00* (2013.01); *A61B 17/00234* (2013.01); *A61B 34/30* (2016.02); *A61B 34/74* (2016.02); *A61B 90/60* (2016.02); *B25J 9/1689* (2013.01); *B25J 13/02* (2013.01); *B25J 13/06* (2013.01); *B25J 13/088* (2013.01); *A47B 21/0314* (2013.01); *A47B 2021/0307* (2013.01); *A47B 2021/0321* (2013.01); *A47B 2021/0392* (2013.01); *A61B 2017/00199* (2013.01); *A61B 2017/00207* (2013.01); *A61B 2017/00225* (2013.01); *A61B 2017/00424* (2013.01); *A61B 2017/00973* (2013.01); *Y10S 901/02* (2013.01)

(58) Field of Classification Search
  CPC ........... A61B 2017/00199; A61B 2017/00225; A61B 34/37; A61B 34/35; A61B 34/76; B25J 9/1689; B25J 13/02; B25J 13/088; Y10S 901/02
  USPC ................................ 606/130; 700/245–264; 318/568.11–568.25
  See application file for complete search history.

(56) References Cited

U.S. PATENT DOCUMENTS

| | | | | |
|---|---|---|---|---|
| 8,508,173 | B2* | 8/2013 | Goldberg | G16H 20/40 318/432 |
| 9,079,089 | B2 | 7/2015 | Lokken et al. | |
| 9,474,580 | B2 | 10/2016 | Hannaford et al. | |
| 9,763,741 | B2* | 9/2017 | Alvarez | A61B 1/018 |
| 9,788,903 | B2* | 10/2017 | Kim | A61B 34/30 |
| 10,219,871 | B2* | 3/2019 | Mirbagheri | A61G 13/06 |
| 10,299,866 | B2* | 5/2019 | Cohen | A61B 34/37 |
| 10,398,519 | B2* | 9/2019 | Kim | A61B 34/76 |
| 10,464,209 | B2* | 11/2019 | Ho | B25J 9/1697 |
| 10,568,704 | B2 | 2/2020 | Savall et al. | |
| 10,912,619 | B2* | 2/2021 | Jarc | G16H 20/40 |
| 10,973,592 | B2* | 4/2021 | Cohen | A61B 34/37 |
| 11,039,889 | B2* | 6/2021 | Frey | A61F 2/30942 |
| 11,132,462 | B2* | 9/2021 | Shelton, IV | G06F 21/6254 |
| 2003/0151288 | A1 | 8/2003 | Deisig | |
| 2004/0111183 | A1 | 6/2004 | Sutherland et al. | |
| 2008/0125794 | A1 | 5/2008 | Brock et al. | |
| 2010/0217991 | A1 | 8/2010 | Choi | |
| 2010/0225209 | A1* | 9/2010 | Goldberg | G16H 20/40 312/209 |
| 2011/0118748 | A1 | 5/2011 | Itkowitz | |
| 2012/0221147 | A1* | 8/2012 | Goldberg | G16H 20/40 700/264 |
| 2013/0030571 | A1 | 1/2013 | Ruiz et al. | |
| 2013/0161988 | A1 | 6/2013 | Lokken et al. | |
| 2014/0121834 | A1 | 5/2014 | Ogawa et al. | |
| 2014/0222023 | A1* | 8/2014 | Kim | A61B 34/30 606/130 |
| 2014/0243849 | A1* | 8/2014 | Saglam | A61B 34/75 606/130 |
| 2014/0276944 | A1* | 9/2014 | Farritor | A61B 34/30 606/130 |
| 2015/0066051 | A1 | 3/2015 | Kwon et al. | |
| 2015/0119638 | A1* | 4/2015 | Yu | A61B 1/018 600/102 |
| 2015/0248847 | A1 | 9/2015 | Wang et al. | |
| 2016/0374541 | A1* | 12/2016 | Agrawal | A61B 1/00009 600/102 |
| 2016/0374771 | A1* | 12/2016 | Mirbagheri | A61G 13/04 606/130 |
| 2017/0333139 | A1* | 11/2017 | Suresh | G16H 40/67 |
| 2018/0078034 | A1 | 3/2018 | Savall et al. | |
| 2018/0078319 | A1 | 3/2018 | Nobles et al. | |
| 2018/0193099 | A1* | 7/2018 | Kim | A61B 34/30 |
| 2018/0214226 | A1 | 8/2018 | Kan | |
| 2018/0271602 | A1* | 9/2018 | Frey | A61B 17/7013 |
| 2019/0090969 | A1* | 3/2019 | Jarc | A61B 34/25 |
| 2019/0105776 | A1* | 4/2019 | Ho | A61B 34/30 |

FOREIGN PATENT DOCUMENTS

| | | |
|---|---|---|
| JP | 10-254381 A | 9/1998 |
| JP | 2006-195058 A | 7/2006 |
| JP | 2007-301071 A | 11/2007 |
| JP | 2013-022651 A | 2/2013 |
| JP | 2016-520334 A | 7/2016 |
| KR | 10-2015-0045469 A | 4/2015 |
| WO | 8501643 | 4/1985 |
| WO | 2011/060139 A2 | 5/2011 |
| WO | 2011/116332 A2 | 9/2011 |
| WO | 2013/012018 A1 | 1/2013 |
| WO | 2014/151621 A1 | 9/2014 |
| WO | WO2018/057814 A1 | 3/2018 |

OTHER PUBLICATIONS

International Search Report & Written Opinion of the International Search Authority dated Dec. 14, 2017 for WO Application No. PCT/US17/052824.
CNET. "This Could Be the Desk of the Future." YouTube, YouTube, Jul. 20, 2016. 0:10, 1:19, 0:52-1:00. www.youtube.com/watchv=UaNf50BAI8U.
Australian Full Examination Report dated Apr. 26, 2019 for related Australian Appln. No. 2017330370 3 Pages.
Decision to Grant a Patent of the Japanese Patent Office dated Nov. 26, 2020 for related Japanese Patent Application No. 2019-511847.
Ex Parte Quayle Action of the U.S. Patent Office dated Aug. 21, 2019 for related U.S. Appl. No. 15/624,579.
Notice of Allowance of the Korean Patent Office dated Feb. 2, 2021 for related Korean Patent Application No. 10-2019-7006152.
Notice of Allowance of the U.S Patent Office dated Nov. 1, 2019 for related U.S. Appl. No. 15/712,052.
Notice of Allowance of the U.S Patent Office dated Oct. 2, 2019 for related U.S. Appl. No. 15/624,579.
Second Office Action of the Chinese Patent Office dated Feb. 23, 2021 for related Chinese Patent Application No. 201780003856.6.
Notice of Final Office Action of the Korean Patent Office dated Aug. 27, 2020 for related Korean Patent Application No. 10-2019-7006152.
Office Action for Chinese Application No. 201780003856.6 dated Sep. 3, 2021, 21 pages.
Examiner's Report of the Canadian Patent Office dated Feb. 10, 2020 for Canadian Patent Application No. 3035251.
Extended European search report of the European Patent Office dated Apr. 23, 2020 for related European Patent Application No. 17853942.5.
First Office Action of the Chinese Patent Office dated Jun. 29, 2020 for related Chinese Patent Application No. 201780003856.6.

(56) References Cited

OTHER PUBLICATIONS

Notice of Reasons for Rejection of the Japanese Patent Office dated Feb. 25, 2020 for related Japanese Patent Application No. 2019-511847.

* cited by examiner

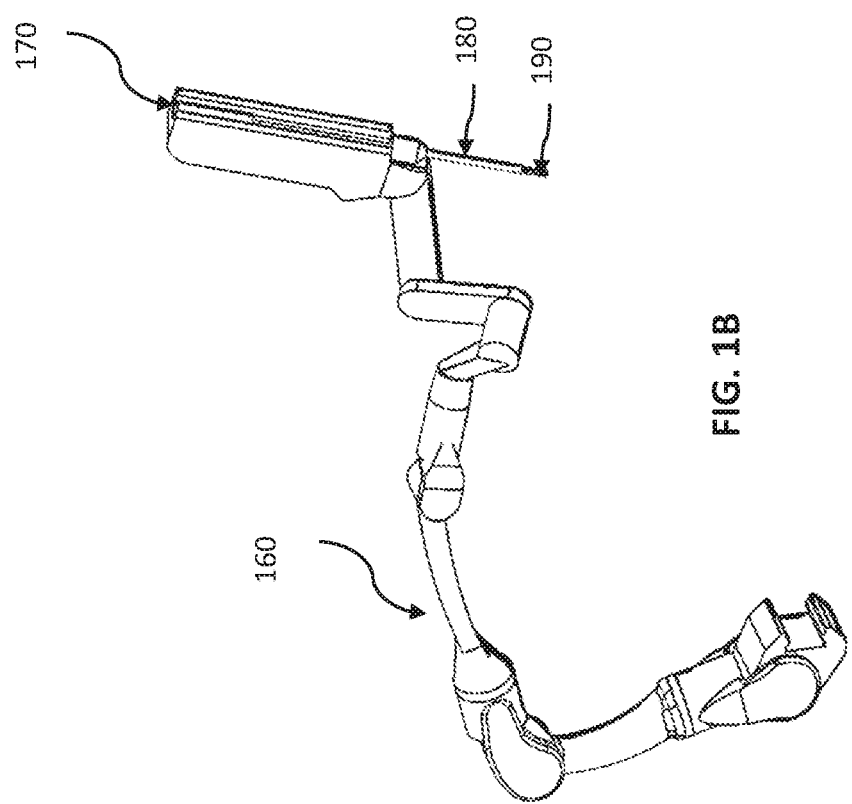

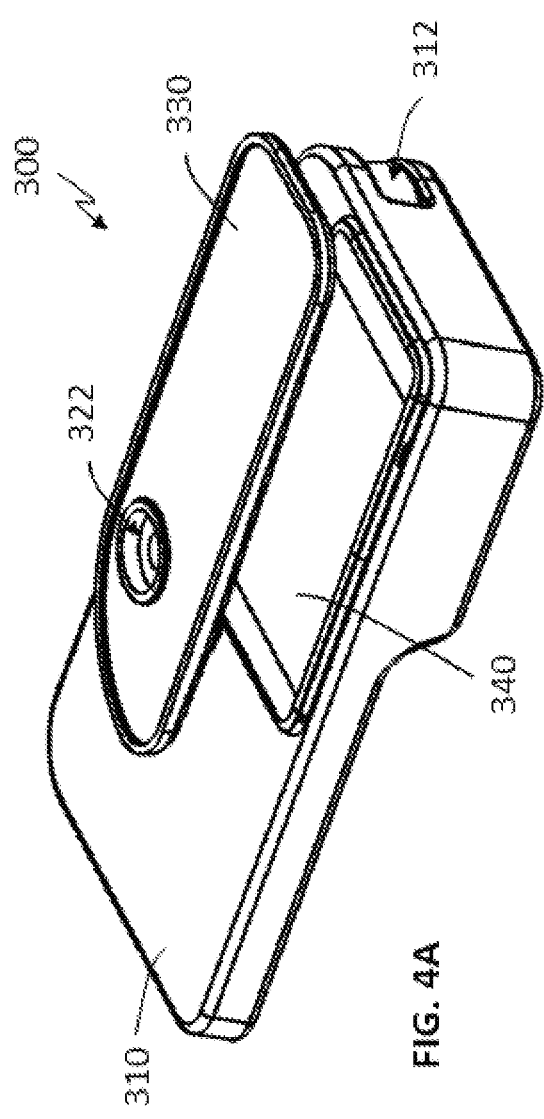
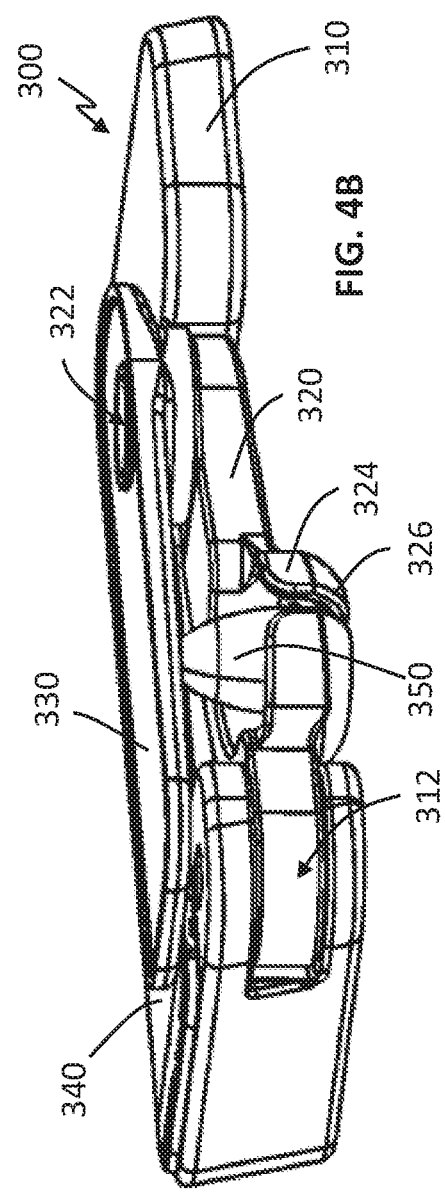

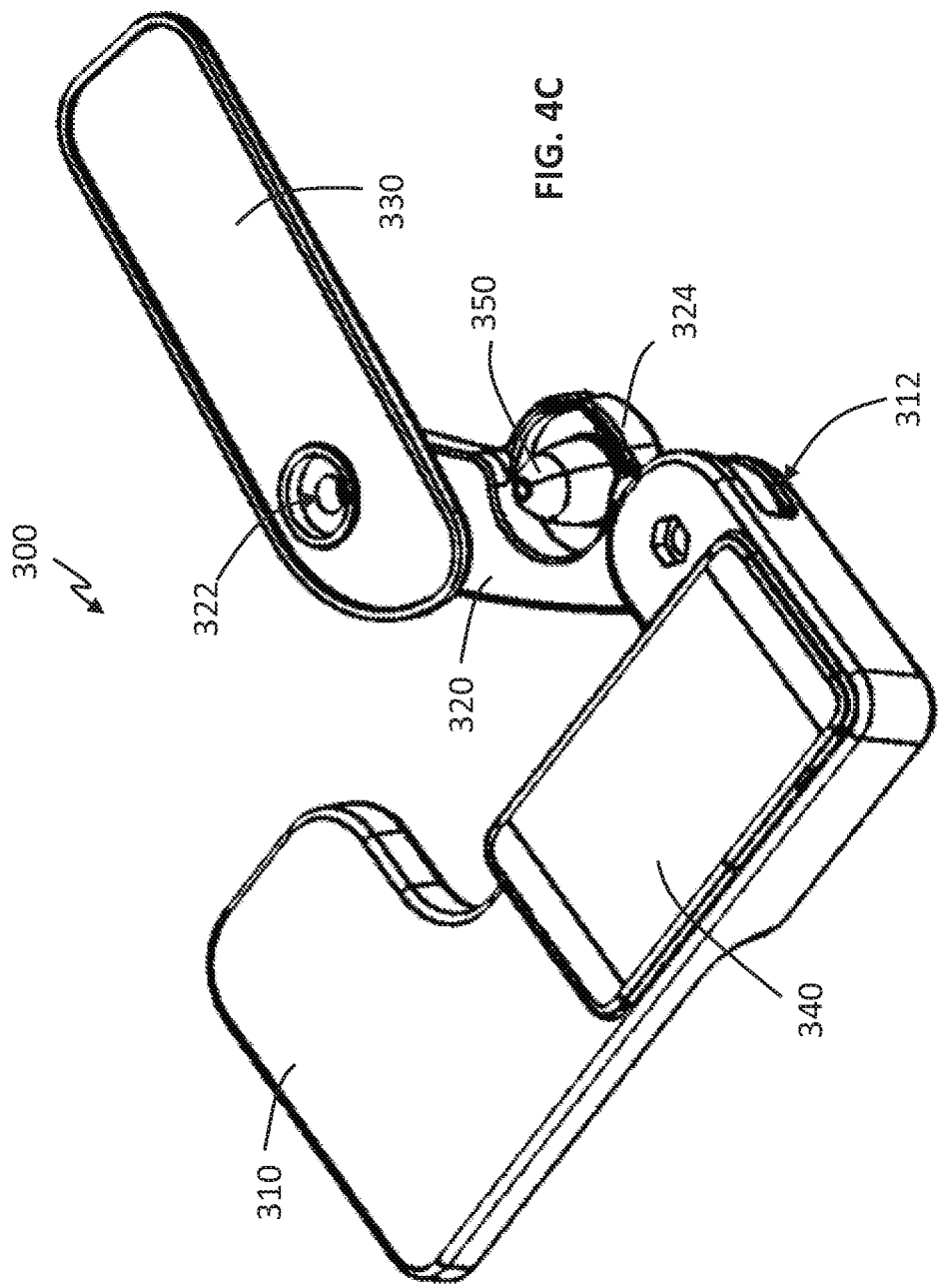

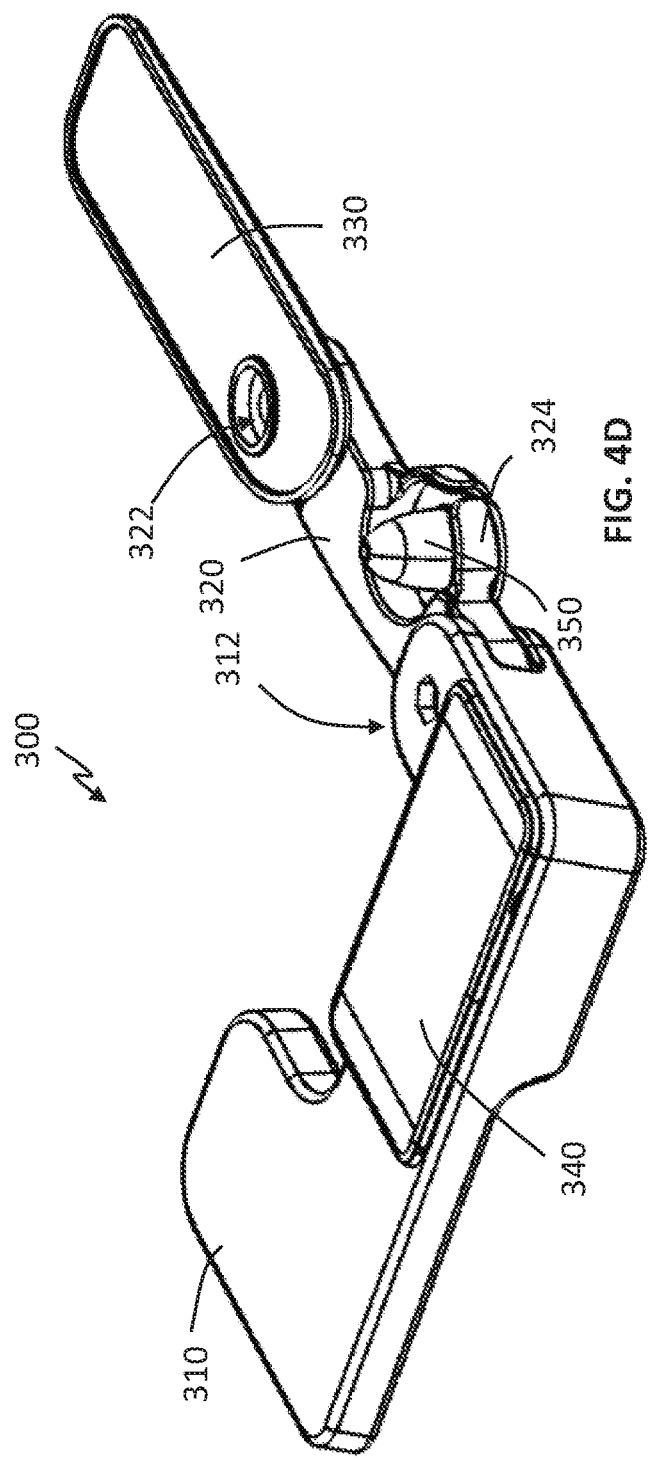

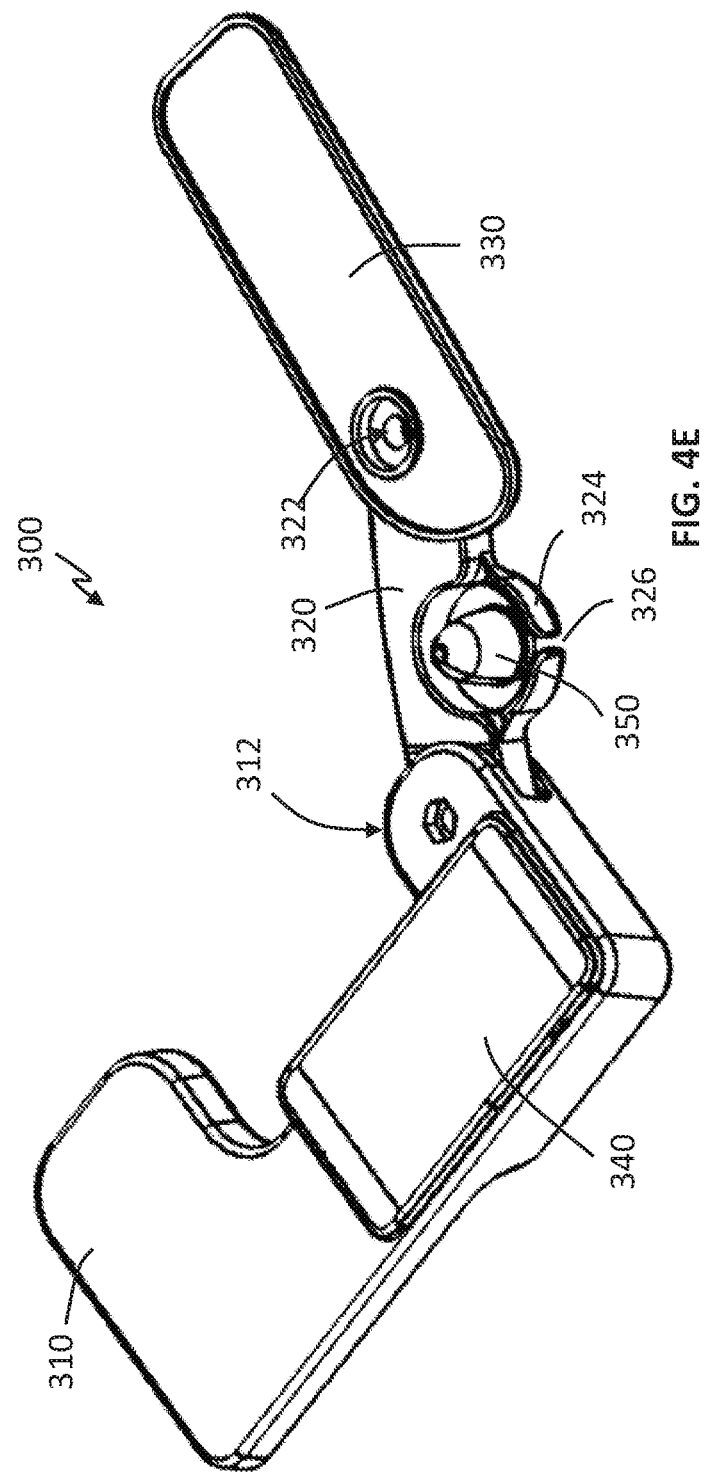

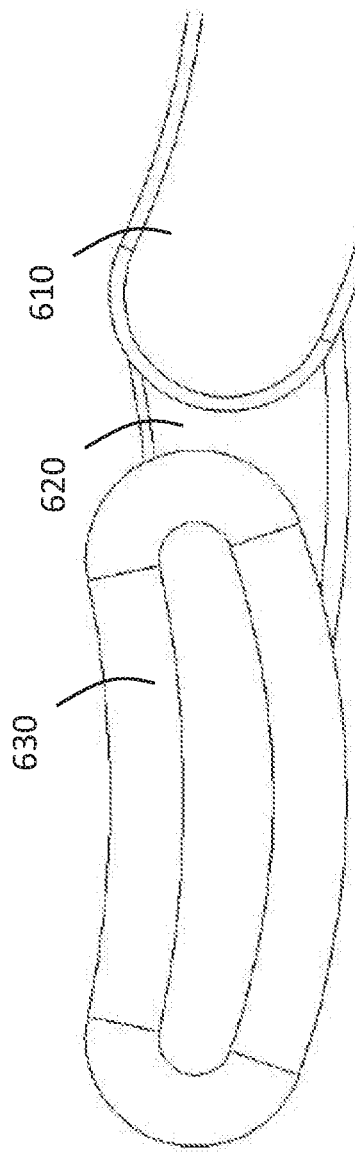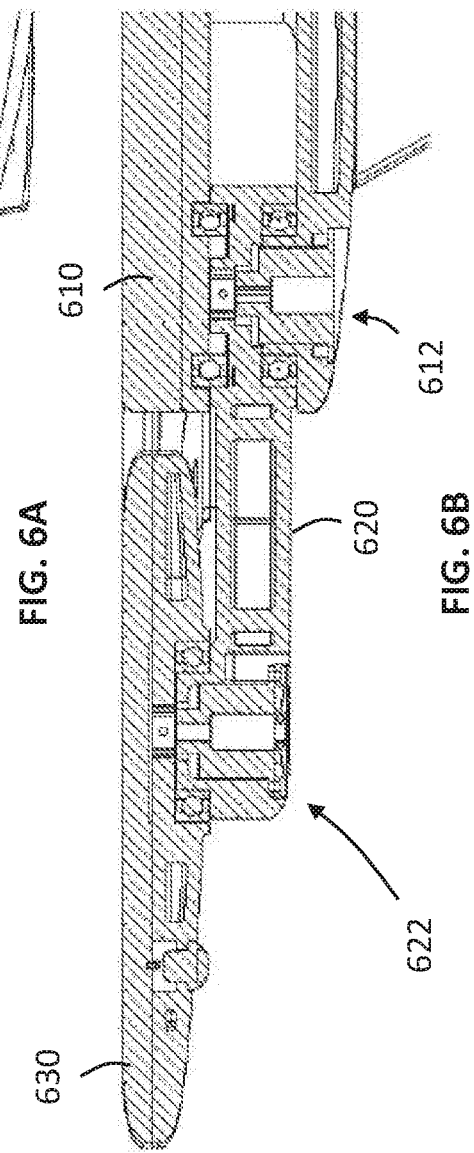
FIG. 6A
FIG. 6B

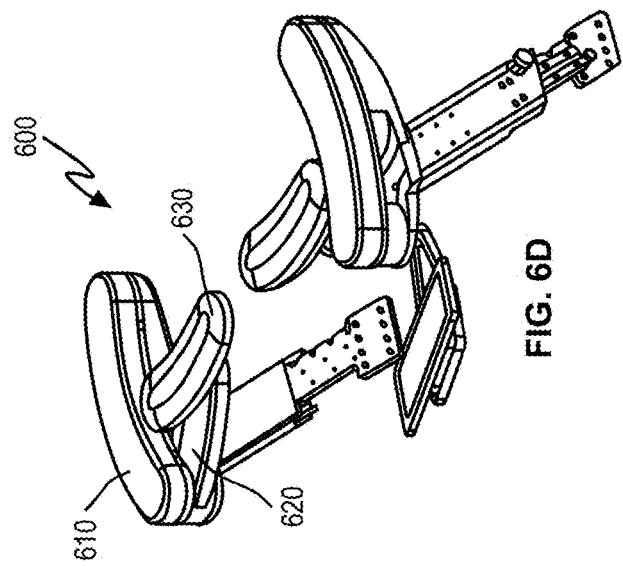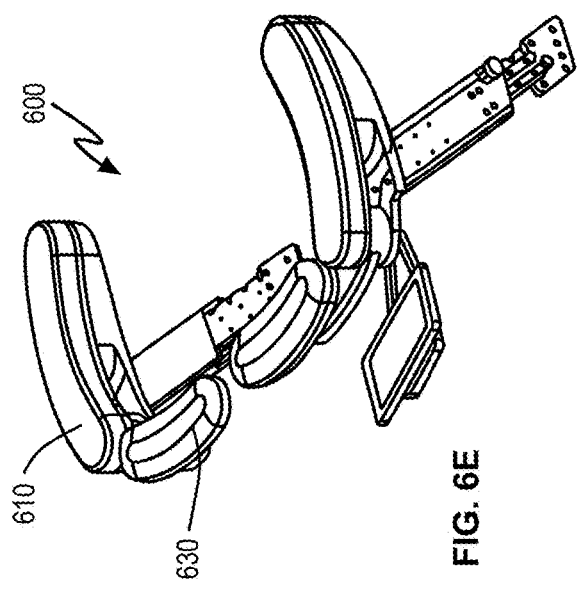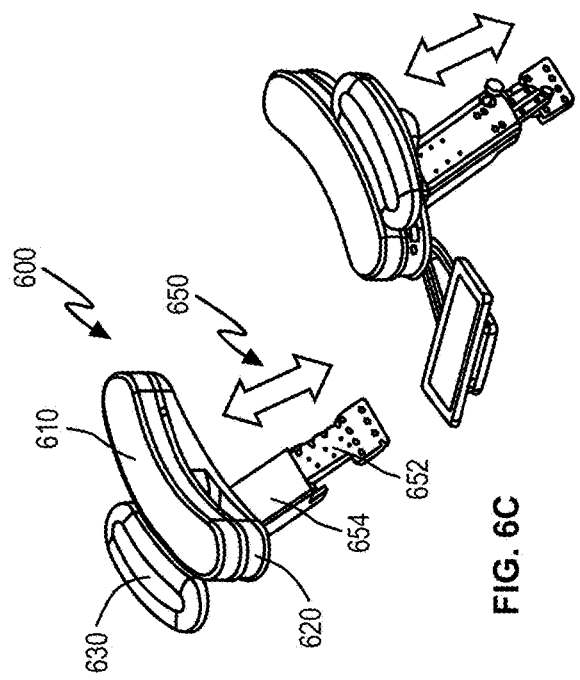

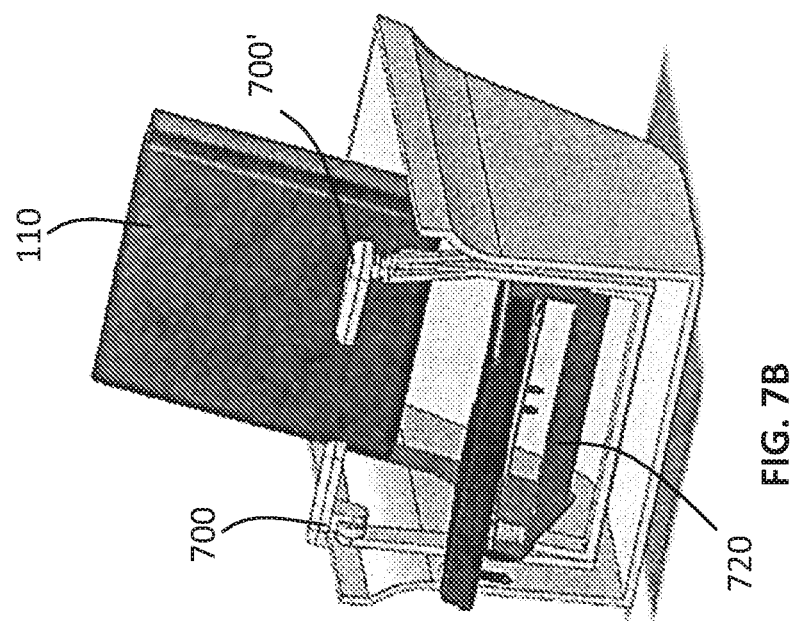
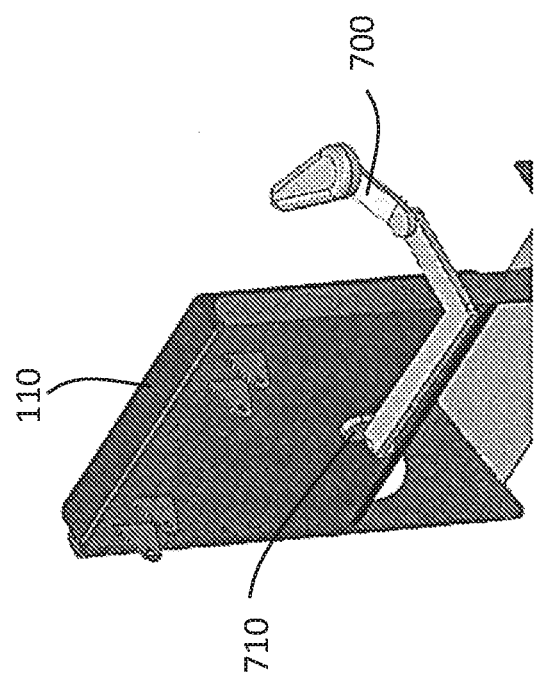
FIG. 7B
FIG. 7A

USER ARM SUPPORT FOR USE IN A ROBOTIC SURGICAL SYSTEM

CROSS-REFERENCE TO RELATED APPLICATIONS

This application is a divisional of U.S. patent application Ser. No. 15/624,579, filed on Jun. 15, 2017, which claims priority to U.S. Patent Application Ser. No. 62/397,823, filed on Sep. 21, 2016, which is hereby incorporated by this reference in its entirety.

TECHNICAL FIELD

This invention relates generally to robotic-assisted systems, and more specifically to new and useful user systems for controlling a robotic surgical system.

BACKGROUND

Minimally-invasive surgery (MIS), such as laparoscopic surgery, involves techniques intended to reduce tissue damage during a surgical procedure. For instance, laparoscopic procedures typically involve creating a number of small incisions in the patient (e.g., in the abdomen), and introducing one or more instruments (e.g., one or more tools, at least one camera, etc.) through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery.

MIS may be performed with non-robotic or robotic systems. Conventional robotic systems, which may include robotic arms for manipulating instruments based on commands from an operator, may provide many benefits of MIS while reducing demands on the surgeon. Control of such robotic systems may require control inputs from a user (e.g., surgeon or other operator) via one or more user interface devices that translate manipulations or commands from the user into control of the robotic system. Such user interface devices may enable a surgeon or other user to operate the robotic system from a remote location (e.g., in teleoperation). Thus, it is desirable to have a user system setup in which the user may operate the user interface devices in an ergonomic and efficient manner.

SUMMARY

Generally, in some variations, a user system for a robotic surgical system may include a handheld groundless user interface device configured to control the robotic surgical system, and a user console. The user console may include a seat and a first adjustable, ergonomic arm support linkage, wherein the first arm support linkage is movable between a folded storage configuration and at least one unfolded use configuration corresponding to at least one of a user characteristic and a surgical task characteristic. The at least one unfolded use configuration may be pre-stored in a database. Exemplary user characteristics include user height, user weight, user girth, etc. Exemplary surgical task characteristics may relate to certain surgical tasks (e.g., causing rotation or translation of a surgical instrument around a longitudinal axis, etc.) that may involve particular characteristic arm movements.

The first arm support linkage may include a plurality of linked segments, including a proximal segment (e.g., which may be coupled to the seat), an intermediate segment coupled to the proximal segment, and a distal segment coupled to the intermediate segment. For example, the arm support linkage may include a SCARA linkage in which the proximal segment and the distal segment rotate within different planes (e.g., parallel and offset planes). The arm support linkage may further include a mount portion for docking the groundless user interface device, such as when the user interface device is not in use. In some variations, the mount portion may be hidden when the first arm support linkage is in the folded storage combination (e.g., coupled to the intermediate segment in such a manner so as to be covered by the distal segment when the arm support linkage is in the folded storage configuration). In some variations, a display may be coupled to the arm support linkage and be used to display relevant information such as system status information, medical imaging, etc. The display may, in some variations, be a touchscreen device to permit input of user information such as a user login and/or user characteristics.

The first arm support linkage may include a plurality of joints connecting the segments. At least one of the joints may be damped (e.g., a frictional joint) and/or include a brake, in order to help maintain a desired configuration of the arm support linkage once the arm support linkage is positioned.

In some variations, the user console may further include a second adjustable arm support linkage. The first and second support linkages may be movable in a synchronized manner, so as to be adjustable in configuration and/or height, etc. in substantially the same manner at substantially the same time.

The system may further include an arm support linkage tracking sensor system configured to detect a configuration (e.g., position, folded, unfolded, etc.) of at least a portion of the first arm support linkage. In some variations, the system may additionally or alternatively include a user tracking sensor configured to detect a user arm position (e.g., contact, relative distance, etc.) relative to the first arm support linkage. Such sensor systems may be useful for characterizing usage of the arm support linkage, such as for storing user preferences, monitoring ergonomics and/or efficiency of use, training purposes, offering changes in the arm support linkage position to improve its usage, etc.

In some variations, the system may further include a clutch arrangement, in which the first arm support linkage includes at least one actuated joint that is actuated to follow a detected user arm position when the clutch arrangement is engaged. For example, when the clutch arrangement is engaged, the arm support linkage may function as a "floating" arm support provides some support to the user's arm while also following the user's arm movements at least in some directions (e.g., a lateral plane).

Generally, a method for operating a user system for a robotic surgical system may include characterizing a usage of an adjustable, ergonomic arm support linkage by a user controlling the robotic surgical system from a user console, wherein the arm support linkage is in a current configuration, identifying from a database a model configuration of the portion of the arm support linkage, wherein the model configuration corresponds to at least one of a user characteristic and a surgical task characteristic; and providing an alert regarding a difference between the current configuration and the model configuration of the portion of the arm support linkage to improve the usage of the arm support linkage by the user.

For example, characterizing the usage of the arm support linkage may include detecting position and/or orientation of the portion of the arm support linkage with an arm support linkage tracking sensor system. Characterizing the usage of the arm support linkage may additionally or alternatively include detecting a user arm position (e.g., contact, distance) relative to the arm support linkage with a user tracking sensor system. The characterization of the usage may be stored in memory, and may be associated with a user characteristic and/or a surgical task characteristic.

In some variations, the method may further include actuating one or more joints in the arm support linkage to assume the model configuration based on the difference between the current configuration and the model configuration. Other actuation of the one or more joints may be performed for other purposes, such as for providing a "floating" arm support.

The method may further include providing an interlock with the arm support linkage. For example, the method may include disabling a user interface device for controlling the robotic surgical system in response to detecting a folded storage configuration of the portion of the arm support linkage (and/or an absence of contact between the user's arm and the arm support linkage). The method may furthermore include enabling the user interface device for controlling the robotic surgical system in response to detecting a suitable unfolded use configuration of the portion for the arm support linkage (and/or a present of contact between the user's arm and the arm support linkage).

BRIEF DESCRIPTION OF THE DRAWINGS

FIG. 1B is a schematic illustration of one exemplary variation of an instrument driver on a robotic arm manipulator.

FIGS. 4A and 4B are perspective views of one exemplary variation of an arm support linkage in a folded configuration. FIGS. 4C-4E are perspective views of the arm support linkage depicted in FIGS. 4A and 4B in exemplary unfolded configurations.

FIGS. 6A and 6B are top and side cross-sectional views of another exemplary variation of an arm support linkage. FIGS. 6C-6E are perspective views of the arm support linkage depicted in FIGS. 6A and 6B in exemplary progressively unfolded configurations.

FIG. 7A is schematic illustration of one exemplary variation of an arm support linkage coupled to a center of a backseat of a user console. FIG. 7B is a schematic illustration of another exemplary variation of arm support linkages coupled underneath a seat of a user console.

DETAILED DESCRIPTION

Examples of various aspects and variations of the invention are described herein and illustrated in the accompanying drawings. The following description is not intended to limit the invention to these embodiments, but rather to enable a person skilled in the art to make and use this invention.

Robotic Surgical System Overview

Figure 1A:
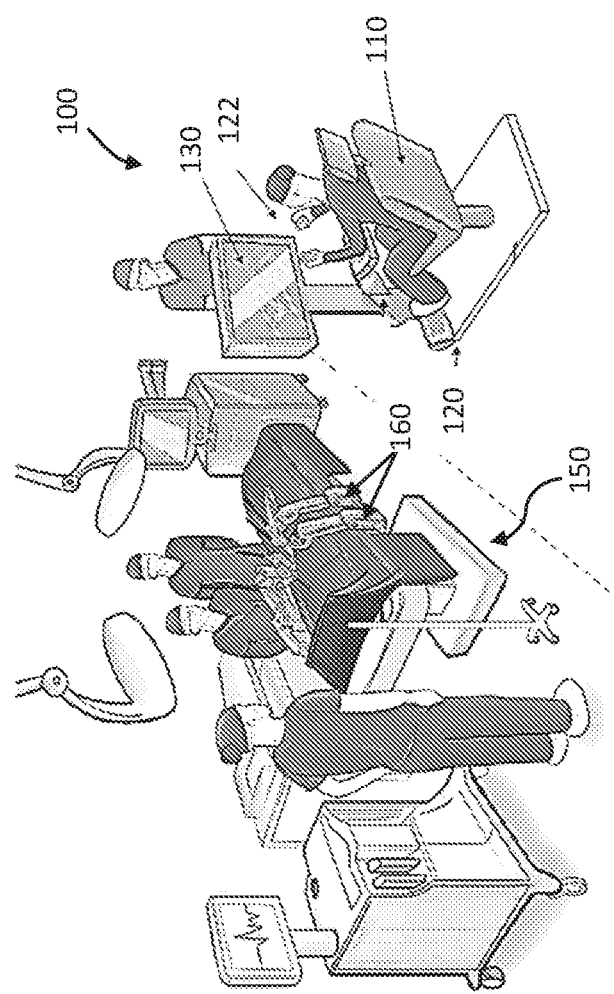
FIG. 1A depicts an example of an operating room arrangement with a robotic surgical system and a surgeon console.

Generally, as shown in FIG. 1A, a user system may interface with a robotic system 150. The robotic system 150 may include one or more robotic arms 160 located at a surgical platform (e.g., table, bed, etc.), where end effectors or surgical tools are attached to the distal ends of the robotic arms 160 for executing a surgical procedure. For example, a robotic system 150 may include, as shown in the exemplary schematic of FIG. 1B, at least one robotic arm 160 coupled to a surgical platform, and a tool driver 170 generally attached to a distal end of the robotic arm 160. A cannula 180 coupled to the end of the tool driver 170 may receive and guide a surgical instrument 190 (e.g., end effector, camera, etc.). Furthermore, the robotic arm 160 may include a plurality of links that are actuated so as to position and orient the tool driver 170, which actuates the surgical instrument 190.

A user (such as a surgeon or other operator) may use the user console 100 to remotely manipulate the robotic arms 160 and/or surgical instruments (e.g., tele-operation). The user console 100 may be located in the same procedure room as the robotic system 150, as shown in FIG. 1A. In other embodiments, the user console 100 may be located in an adjacent or nearby room, or tele-operated from a remote location in a different building, city, or country, etc.

In one example, the user console 100 comprises a seat 110, foot-operated controls 120, one or more handheld user interface devices 122, and at least one user display 130 configured to display, for example, a view of the surgical site inside a patient. For example, as shown in the exemplary user console shown in FIG. 1C, a user located in the seat 110 and viewing the user display 130 may manipulate the foot-operated controls 120 and/or handheld user interface devices to remotely control the robotic arms 160 and/or surgical instruments. For example, the handheld user interface devices may be groundless (and communicating signals with a wired or wireless connection) in that the handheld user interface devices are not coupled to a fixture (e.g., mounted or substantially affixed to a fixed structure). The user console may, in some variations, further include one or more arm supports 140 (e.g., a left-side arm support and a right-side arm support) which may generally be configured to provide support to the arms of the user located in the seat 110 during a surgical procedure. For example, the arm supports 140 may provide an ergonomic resting surface for the user's arms, thereby reducing fatigue. Other exemplary functions of the arm supports 140 are described elsewhere herein.

During an exemplary procedure or surgery, the patient is prepped and draped in a sterile fashion, and anesthesia is achieved. Initial access to the surgical site may be performed manually with the robotic system 150 in a stowed configuration or withdrawn configuration to facilitate access to the surgical site. Once access is completed, initial positioning and/or preparation of the robotic system may be performed. During the surgical procedure, a surgeon or other user in the user console 100 may utilize the foot-operated controls 120 and/or user interface devices 122 to manipulate various end effectors and/or imaging systems to perform the procedure. Manual assistance may also be provided at the procedure table by sterile-gowned personnel, who may perform tasks including but not limited to retracting organs, or performing manual repositioning or tool exchange involving one or more robotic arms 160. Non-sterile personnel may also be present to assist the surgeon at the user console 100. When the procedure or surgery is completed, the robotic system 150 and/or user console 100 may be configured or set in a state to facilitate one or more post-operative procedures, including but not limited to robotic system 150 cleaning and/or sterilization, and/or healthcare record entry or print-out, whether electronic or hard copy, such as via the user console 100.

In FIG. 1A, the robotic arms 160 are shown with a table-mounted system, but in other embodiments, the robotic arms may be mounted in a cart, ceiling or sidewall, or other suitable support surface. The communication between the robotic system 150, the user console 100, and any other displays may be via wired and/or wireless connection(s). Any wired connections may be optionally built into the floor and/or walls or ceiling. The communication between the user console 100 and the robotic system 150 may be wired and/or wireless, and may be proprietary and/or performed using any of a variety of data communication protocols. In still other variations, the user console 100 does not include an integrated display 130, but may provide a video output that can be connected to output to one or more generic displays, including remote displays accessible via the internet or network. The video output or feed may also be encrypted to ensure privacy and all or portions of the video output may be saved to a server or electronic healthcare record system.

In other examples, additional user consoles 100 may be provided, for example to control additional surgical instruments, and/or to take control of one or more surgical instruments at a primary user console. This will permit, for example, a surgeon to take over or illustrate a technique during a surgical procedure with medical students and physicians-in-training, or to assist during complex surgeries requiring multiple surgeons acting simultaneously or in a coordinated manner.

User System

Figure 1C:
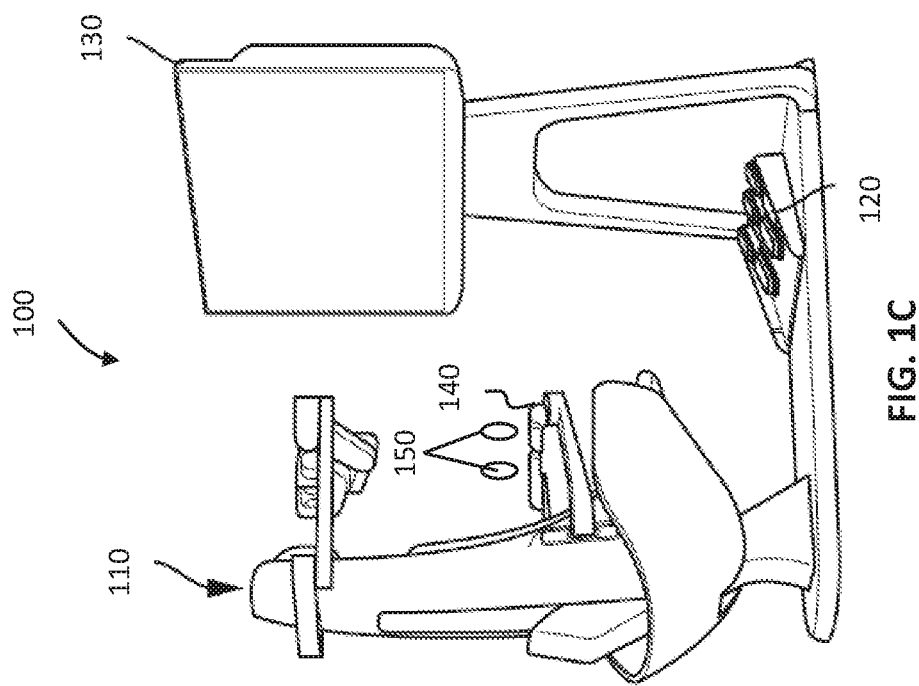
FIG. 1C is a schematic illustration of one exemplary variation of a user console.

Generally, in some variations, as shown in FIG. 1C, a user system for a robotic surgical system may include at least one handheld groundless user interface device 150 configured to control the robotic surgical system, and a user console 100 comprising a seat 110 and an adjustable, ergonomic arm support linkage 140. The arm support linkage 140 may, for example, be coupled to the seat, to the ground (e.g., coupled to a base resting on the ground), or to another portion of the user console. The arm support linkage may be movable between a folded storage configuration and at least one unfolded use configuration. The unfolded use configuration may, for example, correspond to a user characteristic, such as user size (e.g., weight, height, girth, etc.) and/or user preference. As further described herein, the unfolded use configuration may correspond to one or more user characteristics or preferences in accordance with user input, predefined user profiles, etc. As another example, the unfolded use configuration may correspond to a desired surgical task characteristic, such as a particular surgical procedure or portion of a surgical procedure which may ideally provide support to the user's arm at a particular distance from the user's body and/or provide support to different parts of the user's arm, depending on the movement required for the surgical task.

In some variations, the arm support linkage 140 may provide an ergonomic surface upon which a user sitting in the seat 110 may rest his or her arms, thereby reducing fatigue. The arm support linkage 140 may be adjustable to enable optimization of the position of the arm support linkage 140 for various scenarios, such as different kinds of users (e.g., user size) and/or different kinds of surgical tasks and associated arm movements that the user will perform during the course of particular surgical tasks.

Furthermore, the arm support linkage 140 may help provide a grounded reference point (via the user's arm contacting the arm support linkage 140) for the user's arm when the user is handling one or more groundless user interface devices. The grounded reference point may be a location of primary support for the user's arm and/or a location around which a workspace for the user interface device is defined. For example, when used in combination with a groundless user interface device, the arm support linkage may provide a grounded reference point for the user that helps define a workspace within which the user optimally operates the user interface device (e.g., for the type of user, for the type of surgical task, etc.) to improve efficiency of the user's movements, help reduce user fatigue, etc. In other variations, the arm support linkage may be used in combination with a grounded user interface device, such as a user interface device that is permanently mounted to or otherwise affixed to a fixed user console or other fixture.

In some variations, the arm support linkage 140 may be movable between a folded configuration (e.g., for storage) that enables the user to enter and be located in the seat of the user system, and an unfolded configuration (e.g., for use during a surgical procedure) that closes or secures the user into the seat by crossing or wrapping in front of the seated user. In some variations, the system may include one or more tracking sensors (e.g., on the arm support linkage) configured to detect positions including the unfolded configuration of the arm support linkage, such that the arm support linkage may serve as an interlock for controlling the robotic system from the seat. For example the system may disable or prevent control of the robotic surgical system using the user interface devices, as long as the arm support linkage is detected by the tracking sensor to be in the unfolded configuration. Other exemplary aspects of the arm support linkage are described in further detail below.

User Interface Device

User interface devices 150 may be used to control the robotic surgical system. In some variations, a user may use one or more groundless user interface devices 150 configured to be held in the hand of a user and manipulated in free space. For example, the groundless user interface device may be configured to be held between the fingers of a user, and moved about freely (e.g., translated, rotated, tilted, etc.) by the user as the user moves his or her arms, hands, and/or fingers. Additionally or alternatively, the handheld user interface device may be a user interface device coupled to a portion of the user (e.g., to fingers, hand, wrist, and/or arms of a user) directly or via any suitable mechanism such as a glove, hand strap, sleeve, etc., which still enables the user to manipulate the user interface device in free space. Accordingly, a groundless user interface device (as opposed to a user interface device permanently mounted or grounded to a fixture or the like), the user interface device may be ergonomic and provide dexterous control, such as by enabling the user to control the user interface device with natural body movements unencumbered by the fixed nature of a grounded system.

Generally, a user system may include at least two handheld user interface devices (e.g., a first user interface device to be held by a left hand of the user, and a second user interface device to be held by a right hand of the user). In other variations, the user system may include fewer (e.g., one handheld user interface device) or more (e.g., three, four, or any suitable number of handheld user interface devices). Each user interface device may be configured to control a different aspect or feature of the robotic system. For example, a user interface device held in the left hand of the user may be configured to control a designed left-hand instrument (e.g., represented on a left side of a camera view provided to the user), while a user interface device held in the right hand of the user may be configured to control a designed right-hand instrument (e.g., represented on a right side of the camera view).

The handheld user interface devices may include wired connections. For example, as shown in FIG. 2A, in some variations, the handheld user interface devices may include one or more wired connections (e.g., with a wire 250 coupling the user interface device to an external control system). The wires may, for example, provide power to the user interface device 100 and/or carry sensor signals (e.g., from the tracking sensor assembly). As another example, the user interface devices may be wireless and communicate commands and other signals via wireless communication such as radiofrequency signals (e.g., WiFi or short-range such as 400 mm-500 mm range, etc.) or other suitable wireless communication protocol such as Bluetooth.

Figure 2B:
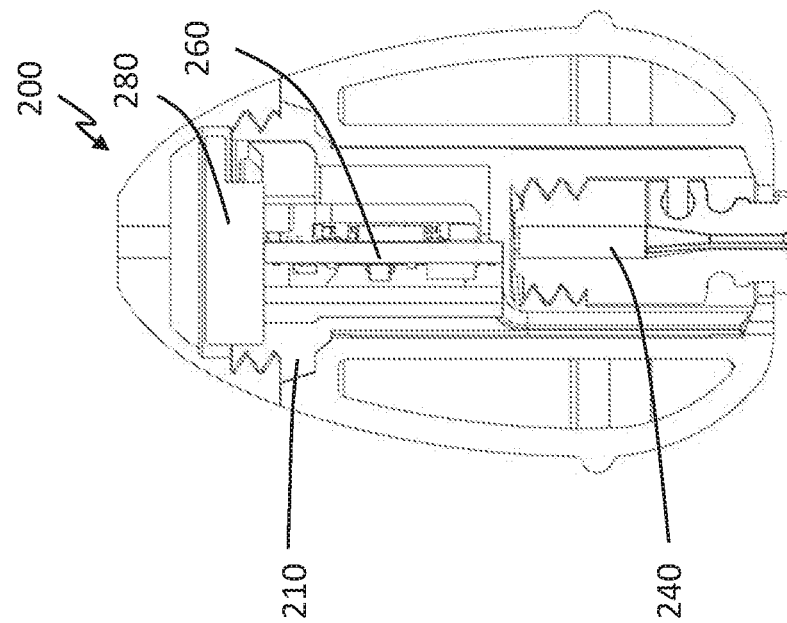
FIG. 2B is a cross-sectional view of the groundless user interface device depicted in FIG. 2A.
Figure 2A:
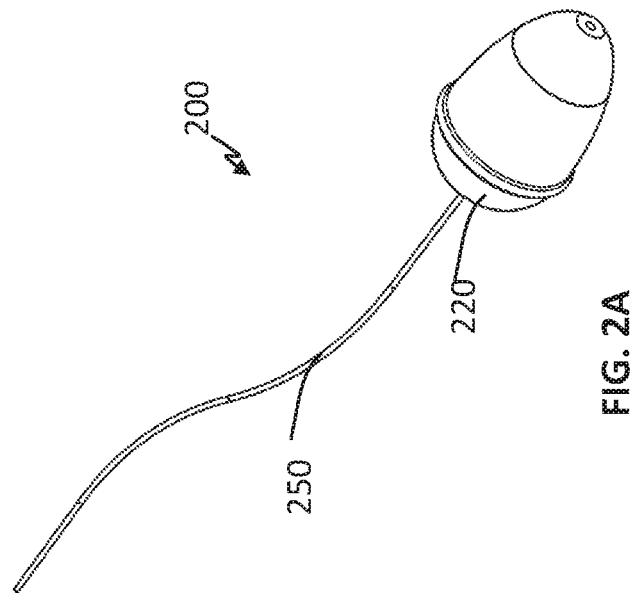
FIG. 2A is a schematic illustration of one exemplary variation of a groundless user interface device for controlling a robotic surgical system.

An exemplary groundless user interface device 200 is shown in FIGS. 2A and 2B. As shown in FIG. 2A, the exemplary user interface device 200 may include a housing 220. The housing may be configured to be held in the hand of a user, and generally may provide a gripping volume with which the user may interface to provide user input commands for controlling the robotic surgical system. For example, at least a portion of the housing 220 may be configured to be grasped, pinched, rolled, squeezed, shaken, or otherwise held or manipulated between fingers of the user's hand. As shown in FIG. 2B, the user interface device 200 may further include a member 210 with the housing 220 at least partially disposed around the member, and a device tracking sensor system 240 configured to detect at least position of the device (e.g., location and/or orientation). The detected position may be correlatable to a control of the robotic surgical system. For example, the user interface device 200 may control at least a portion of a robotic arm, an end effector or tool (e.g., graspers or jaws) coupled to a distal end of the robotic arm, a graphical user interface on a display, or other suitable aspect of feature of the robotic surgical system.

As described above, the housing 220 may generally be configured to be held in the hand of a user. The housing 220 may be compliant and deformable (e.g., by squeezing), where deformation of the housing may be correlatable to a control of the robotic surgical system. For example, squeezing the housing may be correlated to a remote pinching control of an end effector with jaws. In some variations, the housing 220 may include an internal volume or bladder filled with fluid (e.g., air or other gas, silicone oil, saline, water, etc.) or a semi-fluid substance. Additionally or alternatively, the housing 220 may be made at least partially of a flexible material such as silicone, latex, or other suitable polymer or allow.

The member 210 may, in some variations, be disposed along a central, longitudinal axis within the housing 220 such that a device tracking sensor system may be disposed on or within the member 110 and distinguish between location changes of the device due to translation or displacement, and/or orientation changes of the device due to rotation (e.g., roll, pitch, or yaw). Alternatively, in other variations, the member 210 may be disposed in any suitable portion of the housing 220, with a suitable compensation for any offset of the member 210 from an axis of rotation. The member may include a lumen or other internal volume configured to receive various electronics and/or other components, such as at least one printed circuit board 260 having one or more sensors as described below. In some variations, the member 210 may include at least one vibrational motor 280 for providing haptic tactile feedback for indicating particular events, such as movement of the user interface device outside its trackable workspace, etc.

The device tracking sensor system 240 may be configured to detect position (e.g., location and/or orientation) of the user interface device in free space. For example, the device tracking sensor system 240 may include a magnetic tracking probe capable of measuring six degrees of freedom, including physical displacement (e.g., in XYZ space or other suitable coordinate system), roll, pitch, and yaw of the user interface device. Suitable magnetic tracking probes or other sensors are known to those of ordinary skill in the art. The tracking probe may be disposed in the member 210 as shown in FIG. 2B, such as within an internal volume of the member 210, or in any suitable location on the member or housing of the user interface device. Other suitable sensors may be used to track position of the user interface device, such as one or more gyroscopes, one or more accelerometers, and/or one or more magnetometers. For example, some or all such sensors may be part of an inertial measurement unit, or IMU.

Furthermore, the user interface device 200 may include one or more sensors for detecting various kinds of user control inputs and/or other states. For example, one or more sensors may be configured to detect gripping or squeezing of the user interface device, features (e.g., swiping), disconnect from the user (e.g., dropping of the user interface device), etc. which may be correlatable to a control of the robotic surgical system, such as a robotic arm, an end effector, navigation of a graphic user interface display, etc.

In some variations, the user interface device may include one or more squeeze sensors. For example, the user interface device may include one or more proximity sensors, capacitive sensors, pressure sensors, and/or other suitable sensors for detecting user input commands in the form of squeezing, pinching, or other compression the user interface device 200.

In some variations, the user interface device may include one or more gesture detection sensors. For example, the user interface device may include a capacitive sensor configured to detect interaction between the housing and the hand of the user holding the housing. The capacitive sensor may, for example, be used to detect gestures (e.g., swiping, tapping, tapping-and-holding, double-clicking, etc.) used to navigate a graphical user interface or used as a clutch mechanism (e.g., to toggle between control of different aspects of the robotic surgical system).

In some variations, the user interface device 200 may include one or more drop detection sensors configured to determine when the user's hands have disconnected from the user interface device, in order to trigger suspension of communication between the user interface device and control of the robotic surgical system, thereby avoiding inadvertent or unintentional commands to the robotic surgical system. For example, the user interface device may include at least one capacitive sensor (e.g., on the member 210 and/or housing 220) that may be configured to detect when the user's fingers are no longer proximate the housing due to a sudden drop of capacitance below a predetermined threshold. As another example, the user interface device may include at least one accelerometer and/or at least one gyroscope, which may be configured to detect a sudden downward drop due to gravity when the user is no longer holding the user interface device.

Other variations of a groundless user interface device are described in further detail in U.S. Patent Application No. 62/432,538, which is hereby incorporated by this reference in its entirety. However, the groundless user interface devices described herein and in U.S. Patent Application No. 62/432,538 are only exemplary variations that may be used in combination with the user console. Any suitable groundless user interface device may be used with the user console.

User Console

Generally, a user console may provide a highly ergonomic, adjustable system from which a user may comfortably remotely control (e.g., in teleoperation) a robotic surgical system. Exemplary variations of a user console are described in U.S. Patent Application No. 62/397,823, which is hereby incorporated by this reference in its entirety. For example, the user console may be adjustable (e.g., automatically and/or manually) according to a profile associated with the user, surgical task or procedure, and/or other parameters or settings. In some variations, as shown in FIG. 1C, a user console may include a seat 110 and an adjustable, ergonomic arm support linkage 140 coupled to the seat. For example, the seat 110 may be adjustable to provide for various user positions, such as a seated configuration, a reclined configuration, an elevated configuration, and/or other seat configurations, as described further in U.S. Patent Application No. 62/397,823. As another example, the seat 110 may be adjustable for different user types (e.g., sizes, such as height, weight, girth, etc.) and/or surgical tasks. Furthermore, in some variations, the arm support linkage 140 may be similarly adjustable for different seat configurations, different user types and/or surgical tasks, as described below.

As shown in FIG. 1C, the user console 100 may further include one or more foot-operated controls 120 for controlling the robotic surgical system and/or the user console. For example, a foot-operated control may be used to control an end effector (e.g., pinching, grasping, cutting, etc.) on the end of a robotic arm. As another example, a foot-operated control may be used to control part of the user console, such as for adjusting the position of the seat assembly (e.g., transitioning between a seated configuration, a reclined configuration, an elevated configuration, and/or other seat configurations), arm support assembly, displays, etc. The foot-operated controls 120 may include, for example, a pedal assembly including one or more actuatable foot pedals, foot switches, touchpads, force plates, joysticks, and/or other suitable foot-operated mechanisms. The position of the foot-operated controls 120 may be adjusted for ergonomic purposes, as described further in U.S. Patent Application No. 62/397,823

In some variations, the user console 100 may include one or more displays for providing and/or receiving information from a user. At least one display may be coupled, for example, to the arm support linkage as described below. As another example, the user console 100 may include an open display 130 positioned in front of the seat 110. The one or more displays may, for example, be configured to receive real-time or near real-time surgical information. For example, the one or more displays may receive and show video feed from a camera instrument inserted in a body cavity of the patient, where the camera instrument may provide a field of view of the surgical site, such as during a surgical procedure utilizing end effectors controlled via the user console. As another example, the one or more displays may show patient medical images, patient vital signs, a graphical user interface, etc. The position of the open display 130 may be adjusted for ergonomic purposes, as described further in U.S. Patent Application No. 62/397,823

Arm Support

Figure 3B:
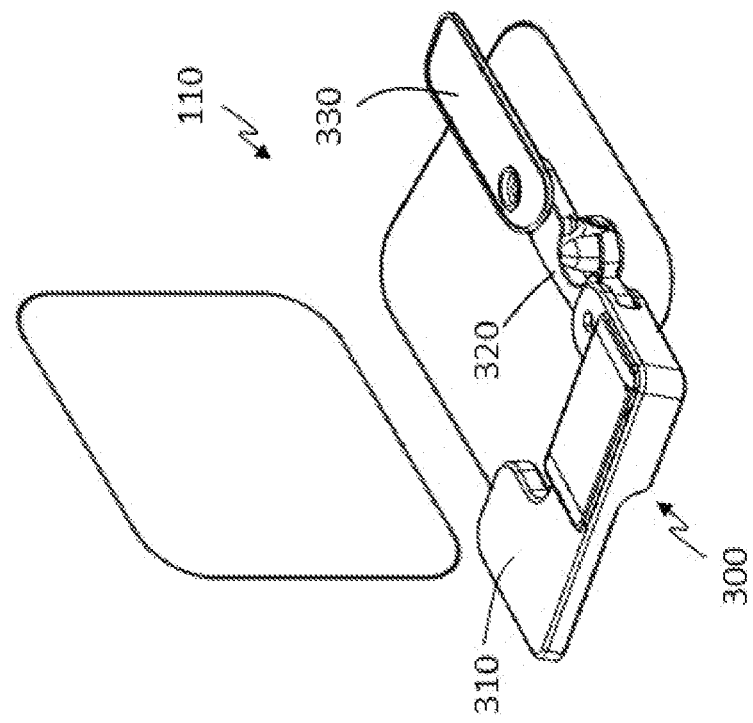
FIG. 3B is a schematic illustration of the arm support linkage depicted in FIG. 3A, in an exemplary unfolded configuration.
Figure 3A:
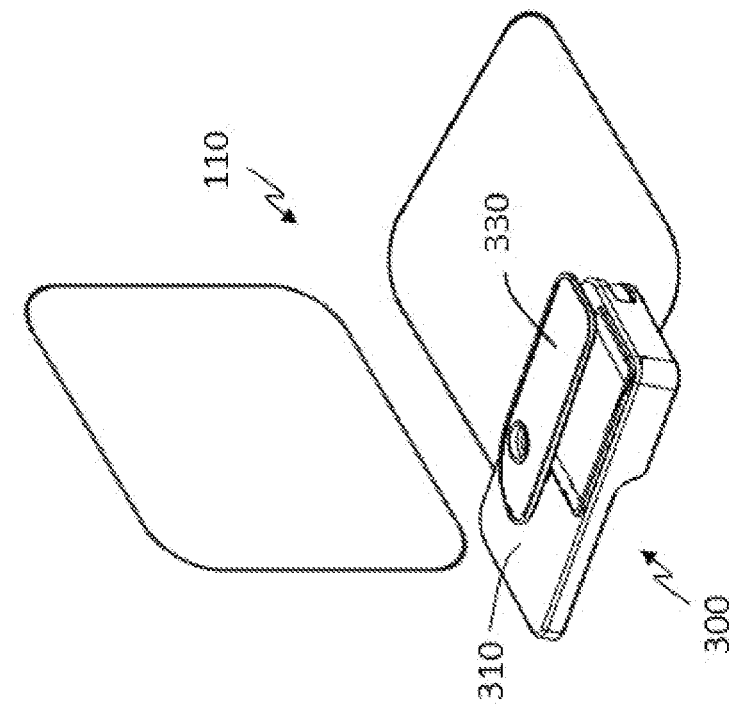
FIG. 3A is a schematic illustration of one exemplary variation of an arm support linkage adjacent a user console seat, with the arm support linkage in an exemplary folded configuration.

As shown in FIGS. 3A and 3B, an arm support linkage 300 may be coupled to or adjacent a seat 110. The arm support linkage 300 may be movable between a folded configuration (FIG. 3A) and at least one unfolded configuration (e.g., FIG. 3B). For example, the folded configuration may be suitable for permitting a user to enter and exit the user console, or for purposes of storage and/or transport, etc.

One or more various unfolded configurations may correspond to a desired position of the arm support for a user, depending on a user characteristic (e.g., user size such as height, weight, or girth) and/or a surgical task characteristic (e.g., type of surgical procedure that the user is performing with the robotic surgical system). Generally, the unfolded arm support may be configured with adjustable arm support height, anterior/posterior position, and/or medial/lateral rotation, and where separate left/right arm supports are provided, each arm support may be independently configurable. The adjustable arm support features may be manually adjustable by the user and/or motorized, and may be computer-controlled. Adjusted arm support configurations and settings may be stored in memory as part of a profile associated with a particular user and/or type of user, with the configuration(s) or profile configured to be stored and recalled via a seat controller. Access to the seat controller may be performed, for example, through a user display or touchscreen.

One or more of the unfolded configurations may furthermore help provide an enclosure in front of the user when the user is positioned in the seat 110, thereby securing the user in the seat 110. Although FIGS. 3A and 3B depict only one arm support linkage 300 adjacent to the seat 110, it should be understood that in some variations, at least two arm support linkages may be adjacent to the seat 110. For example, the user system may include first and second arm support linkages coupled to or otherwise adjacent to opposite sides of the seat 110. The first and second arm support linkages may be mirrored versions of each other (e.g., a left-side arm support linkage and a mirrored right-side arm support linkage which unfold generally toward the centerline of the seat 110)

Arm Support Linkage Segments and Configurations

As shown in FIGS. 4B-4E, in some variations an arm support linkage 300 in a user console may include a linkage assembly including a proximal segment 310, an intermediate segment 320, and a distal segment 330. The proximal segment 310 may be attached to the seat 110 (e.g., on the side of the seat 110, with a wraparound fixture to a backset of the seat 110, or with a wraparound fixture to an underside of the seat 110, etc.), either directly or through an intervening base structure such as one or more additional proximal segments that attaches to the seat 110 in a similar manner. In other examples, the arm support linkage 140 may be coupled to the ground (e.g., coupled to a base resting on the ground), or to another portion of the user console. In some variations, the linkage assembly may include fewer or more segments. The segments may be connected by pivotable joints. For example, the proximal segment 310 and the intermediate segment 320 may be coupled at joint 312 such that the proximal and intermediate segments may move relative to one another at joint 312. Similarly, the intermediate segment 320 and the distal segment 330 may be coupled at joint 322 such that the intermediate and distal segments move relative to one another at joint 322. Accordingly, articulation of the joints 312 and 322 may enable the arm support linkage to move between folded and unfolded configurations as desired.

In some variations, the arm support linkage may include a SCARA (Selective Compliance Assembly Robot Arm) linkage that is articulated along parallel axes, such as parallel axes passing through joints 312 and 322 (e.g., such that the arm support linkage is generally compliant in an X-Y direction via rotation around the parallel axes but substantially rigid in a Z-direction). For example, as shown in FIGS. 4A-4E, the intermediate segment 320 may rotate relative to the proximal segment 310 via joint 312 in an X-Y direction, and the distal segment 330 may rotate relative to the intermediate segment 320 via joint 322 in an X-Y direction. However, joints 312 and 322 are shown in FIGS. 4A-4E as pin joints collectively providing 2 degrees of freedom, such that joints 312 and 322 substantially prevent movement of the intermediate segment 320 and the distal segment 330 in a Z-direction. In other variations, the arm support linkage may include any suitable kind of linkage (e.g., providing three or more degrees of freedom, including telescoping linkage segments, etc.).

In some variations, all of the segments of the arm support linkage may generally rotate within the same plane. In other variations, at least one segment of the arm support linkage may generally rotate in a separate respective plane (e.g., that is offset from other segments with spacers, etc.). For example, as shown in FIGS. 4A-4E, the proximal segment 310 and the intermediate segment 320 may generally be rotatable in the same plane, while the distal segment 330 may generally be rotatable in a different plane than the proximal segment 310 and the intermediate segment 320. In other words, the intermediate segment 320 may rotatable within a first plane via the pin joint 312, and the distal segment 330 is rotatable within a second plane via the pin joint 322, where the second plane is parallel and offset from the first plane. In other variations, the arm support linkage may include any suitable linkage (e.g., a linkage that is articulable in at least two orthogonal planes).

FIGS. 4A and 4B illustrate an exemplary folded configuration of the arm support linkage 300. Generally, in the folded configuration, the intermediate segment 320 and the distal segment 330 may collapse against the proximal segment 310 (e.g., in a nesting manner) into a more compact arrangement. Adjacent segments (e.g., the proximal segment 310 and the intermediate segment 320, or the intermediate segment 320 and the distal segment 330) may have spatially complementary shapes so as to allow segments to collapse into a smaller volume (e.g., without vertical stackup which may increase storage volume). For example, the proximal segment 310 may be generally "L"-shaped (with a generally rectangular cutout, as shown in FIG. 4C) and provide a generally rectangular space for the generally rectangular intermediate segment 320 to occupy when the arm support linkage is in the folded configuration, thereby allowing the intermediate segment 320 to more compactly fold against the proximal segment 310. As another example, the proximal segment 310 may include a generally arcuate cutout (e.g., circular cutout) and provide a generally circular space for a generally circular intermediate segment to occupy when the arm support linkage is in the folded configuration. As yet another example, the proximal segment 310 and the intermediate segment 320 may be generally arcuate and nest against each other. Other suitable cutout or curved shapes on either the proximal segment 310 or the intermediate segment 320 may facilitate a similarly nested, compact folded configuration. In other variations, a smaller volume for the arm support in the folded configuration may be achieved by stacking the proximal and intermediate segments at least partially vertically, instead of side-by-side as shown in FIGS. 4A and 4B.

Additionally or alternatively, at least one of the segments in the arm support linkage 300 may at least partially overlie another segment so as to allow segments to collapse into a smaller volume. For example, as shown in FIGS. 4A and 4B, the distal segment 330 may at least partially overlie the proximal segment 310 and the intermediate segment 320. Furthermore, having at least one segment overlie another segment may, for example, help provide an edge surface (e.g., the lateral raised edge of the distal segment 330 shown in FIG. 4A closer to the display 340) that a user may more easily grab in order to manually move the arm support linkage toward an unfolded configuration. Additionally or alternatively, the distal segment 330 or other suitable segment may include a raised surface (e.g., ridge, raised cushion, etc.) to help provide a surface for a user to grab.

As shown in FIG. 2A, the arm support linkage 300 may collapse into its folded configuration at a lateral side of the seat 110. In variations including two arm support linkages 300, one arm support linkage may collapse into its folded configuration on a left side of the seat 110, and the other arm support linkage may collapse into its folded configuration on a right side of the seat 110, thereby enabling a user to enter or exit the seat 110 by passing between the pair of folded arm support linkages. In other variations, the arm support linkage may additionally or alternatively collapse into its folded configuration in other locations such as overhead the seat 110, under the seat 110, or in other suitable locations. In some variations, the arm support linkage 300 may collapse into its folded configuration with manual manipulations by a user and/or automatic actuation of joints (e.g., as a predetermined trajectory of the arm support linkage 300, joints folding in sequence one-by-one or simultaneously, etc.).

FIGS. 4C-4E illustrate different exemplary unfolded configurations of the arm support linkage, which provide progressively more space for a user sitting in the seat 110 (e.g., for accommodating different user sizes). FIG. 4C shows the arm support linkage 300 in a first unfolded configuration in which the intermediate segment 320 and the distal segment 330 are extended inward (medially) to open the arm support linkage 300. The distal segment 330 is oriented at a first anterior position to provide support to a user's arm resting on the distal segment 330 and/or help secure the user into the seat 110. FIG. 4D shows the arm support linkage 300 in a second unfolded configuration in which the intermediate segment 320 and the distal segment 330 are further extended inward to further open the arm support linkage 300. The distal segment 330 is oriented at a second anterior position (further frontward than the first anterior position) to provide arm support and/or securement of a larger user. FIG. 4E shows the arm support linkage 300 in a third unfolded configuration in which the intermediate segment 320 and the distal segment 330 are even further extended to further open the arm support linkage 300 even more than the configurations shown in FIGS. 4C and 4D. The distal segment 330 is oriented at a third anterior position (further frontward than the first and second anterior positions) to provide arm support and/or securement of a larger user. Other unfolded configurations may be possible. For example, it should be understood that in some variations, the intermediate segment 320 and the distal segment 330 may be positioned in continuous ranges of motion, such that the arm support linkage 300 may be positioned in any suitable unfolded configurations ranging between those shown in FIGS. 4C-4E. In other variations, the intermediate segment 320 and/or the distal segment 330 may be positioned in any of a set of discrete positions (e.g., via detents in the joints 312 and/or 322), such that the arm support linkage 300 may be securely positioned in a finite number of unfolded configurations. In some variations, the arm support linkage 300 may extend into its unfolded configuration with manual manipulations by a user and/or automatic actuation of joints.

Figure 5:
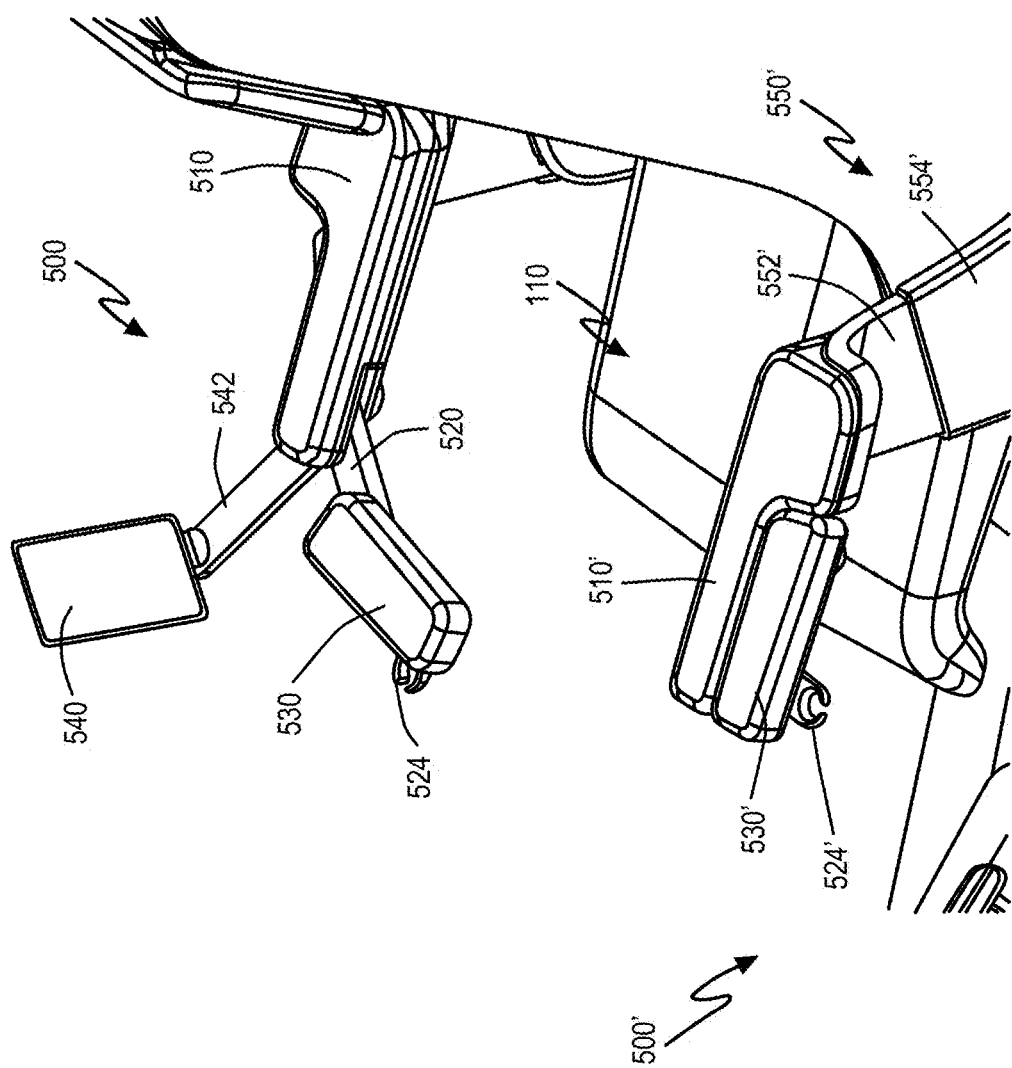
FIG. 5 is a schematic illustration of another exemplary variation of arm support linkages adjacent a user console seat.

In some variations, the distal segment may be located more medially than the proximal segment in the folded configuration. For example, as shown in FIGS. 4A-4E, to move between a folded configuration and an unfolded configuration, the distal segment 330 may unfold from a medial or inner side of the proximal segment 310. In other variations, the distal segment may be located more lateral than the proximal segment in the folded configuration. For example, as shown in FIG. 5, arm support linkage 500' in a folded configuration includes a distal segment 530' folded against a lateral or outside side of the proximal segment 510'. As illustrated by similar arm support linkage 500, to move between the folded configuration and an unfolded configuration, the distal segment 530 may unfold or swing around from the lateral side toward the medial or inner side of the proximal segment 510.

FIGS. 6A-6E illustrate another variation of an arm support linkage 600. The arm support linkage 600 includes a proximal segment 610, an intermediate segment 620 coupled to the proximal segment 610, and a distal segment 630 coupled to the intermediate segment 620. As shown in FIGS. 6A and 6B, the intermediate segment 620 is coupled to the proximal segment 610 via a clevis-style pin joint 612. A generally central portion of the distal segment 630 is coupled to the intermediate segment 620 via a pin joint 622, leaving enough clearance for the distal segment 630 to fully rotate around joint 622 without physically interfering with the proximal segment 610. In the folded configuration shown in FIG. 6C, the distal segment 630 may be generally adjacent to a lateral side of the proximal segment 610, with the intermediate segment 620 at least partially nested within the proximal segment 610 to help facilitate a more compact configuration. At least some of the segments, such as the proximal segment 610 and the distal segment 630, may be curved or contoured similar to each other to help facilitate a compact arrangement. FIG. 6D illustrates a first unfolded configuration in which the intermediate segment 620 and the distal segment 630 have swung around the front of the proximal segment 610 until the distal segment 630 is extended medially and oriented across the user in a first anterior position. FIG. 6E illustrates a second unfolded configuration in which the distal segment 630 is oriented in a second anterior position (further frontward than the first anterior position shown in FIG. 6D) to provide arm support and/or securement of a larger user.

In some variations, the arm support linkage may include a mount portion for docking at least one user interface device. For example, a user interface device may be placed in the mount portion when the user (e.g., surgeon) desires to take a break from teleoperating the robotic surgical system with the user interface device (e.g., to rest or to switch between different operating techniques), and/or for storage or transportation purposes. As shown in FIGS. 4B-4E, an arm support linkage 300 may include a mount portion 324 coupled to the intermediate segment 320. The mount portion 324 may include a cradle, tray, recess, hook, or other receptacle for receiving the user interface device. The mount portion 324 may be integrally formed (e.g., through injection molding) with the intermediate segment 320, or may be formed separately and coupled to the intermediate segment 320 via fasteners, threads, snap-fit, other suitable interference fit, or in any suitable manner. In other variations, the mount portion may be integrally formed with or coupled to any other suitable portion of the arm support linkage or user console. For example, as shown in FIG. 5, the arm support linkage 500 may include a mount portion 524 located on the distal segment 530. In other examples, the mount portion may be located on the proximal segment 510, or another portion of the user console (e.g., on a tray or stand near the seat and accessible by the user sitting in the seat). In some variations, the mount portion (or another portion proximate the mount portion) may include one or more sensors for detecting whether a user interface device is docked in the mount portion. For example, proximity sensors, electromagnetic sensors interacting with the user interface device, or any suitable sensor may be used to determine whether a user interface device is docked. In variations in which the user console includes mounting locations for more than one user interface device (e.g., more than one docking location on a single arm support linkage, or more than one arm support linkage each with a respective docking location), the one or more sensors may be used to detect which of the multiple user interface devices are docked and/or whether all of the multiple user interface devices are docked. The one or more sensors may additionally or alternatively determine whether a user interface device is properly docked (e.g., in a secure manner, or with a left-side user interface device docked on a left-side arm support linkage and a right-side user interface device docked on a right-side arm support linkage).

The mount portion may be hidden (e.g., relatively inaccessible to the user) when the arm support linkage is in the folded configuration and exposed (e.g., relatively accessible to the user) when the arm support linkage is in the unfolded configuration. Since the user may be required to unfold the arm support linkage in order to expose the user interface device and enable the user to retrieve the docked user interface device, such a selectively hidden mount portion may, for example, encourage or remind the user to use the arm support linkage in its unfolded configuration when using the user interface device for control a robotic surgical system, thereby improving ergonomics, reducing user fatigue, etc. and providing other advantages as described herein.

Generally, the arm support segments may be made of any suitable rigid or semi-rigid materials, such as rigid or semi-rigid plastics or metals. The arm support linkage may, for example, by injection molded, 3D printed, machined, casted, or made in any suitable manner. As described in further detail below, the arm support segments may further include cushioning padding, etc. for comfort and/or ergonomics.

Joints and Adjustments

As described above, the segments in the arm support linkage may be connected by a series of adjustable joints (e.g., pin joints 312 and 322, as shown in FIGS. 4A-4E). The arm support linkage may include at least one brake associated with a joint. The brake may be disengaged to allow rotational adjustment of the associated joint, and engaged to lock the joint into a particular rotational position (and help lock at least part of the arm support linkage into a particular configuration, such as a folded configuration or a selected unfolded configuration). The brake, for example, may be electronically controlled, such as with a switch, button, foot pedal (e.g., in the user console), input into the user interface device (e.g., gesture or other input), or other suitable control. Additionally or alternatively, the brake may be a manual brake, such as a latch or clamp, which may be manually controlled. In an exemplary use scenario, the user may disengage one or more brakes in one or more joints of the arm support linkage, manipulate an arm support linkage into a desired unfolded configuration (e.g., suitable to provide a stable support to the user's size and/or preferences, and/or surgical task or procedures to be performed by the user), then engage the one or more brakes to lock the arm support linkage in the desired configuration. After the surgical procedure, or when the user wishes to exit the seat, the user may disengage the one or more brakes, manipulate the arm support linkage into a folded configuration, then re-engage the one or more brakes to lock the arm support linkage into the folded configuration (or optionally leave the brakes disengaged to loosely keep the arm support linkage in the folded configuration). The one or more brakes, when engaged, may be overcome or overridden by application of a sufficient threshold force and/or with a fail-safe command (e.g., provided by a button, switch, trigger, etc.), such as in cases of emergency requiring the user to exit the seat quickly.

Additionally or alternatively, in some variations, the arm support linkage may include at least one damped joint. A damped joint may have a specific resistance to movement (e.g., in-plane movement) at least during use during teleoperation of the robotic surgical system. The damped joint may, upon application of a threshold force sufficient for overcoming the resistance to movement, allow the position of the arm support linkage to be adjusted. For example, at least some of the joints may be damped mechanically (e.g., due to friction or a suitable damping mechanism). In some variations, damped joints may be used without brakes, such that resistance provided in the damped joint serves the similar purpose in substantially locking the arm support linkage into a desired configuration. In other variations, damped joints may be used in combination with brakes (e.g., for reinforced or redundant locking of the arm support linkage into a desired configuration).

In some variations, the arm support linkage may additionally or alternatively include at least one joint movable with an actuator, to enable powered adjustment of the joint and at least a portion of the arm support linkage. Suitable actuators include, but are not limited to, a servomaotor or stepper motor (or other suitable rotary actuator) in combination with an encoder, geartrain, force or torque sensors, etc. Actuated joints may, for example, automatically adjust at least a portion of the arm support linkage to desired or commanded configurations according to a user profile or presets such configurations may be stored in system memory associated with a particular user login, associated with a particular user size, associated with particular one or more surgical tasks, etc., such that upon entry of user or task information, the arm support linkage may be automatically moved to a suitable configuration via the actuated joints. For example, a particular configuration may be recalled from a system memory and the joints of the arm support linkage may be actuated to effect the particular configuration of the arm support linkage (e.g., sequentially or simultaneously in one or more predetermined joint trajectories). Additionally or alternatively, the arm support linkage may be automatically moved to a folded storage configuration via the actuated joints upon an indication that the user wishes to exit the seat.

In another application of powered joints, in some variations, the arm support linkage may provide a "floating" arm support that follows the arms of the user as the user moves his or her arms. A "floating" arm support linkage may provide support to the user's arm in a Z-direction (e.g., vertical direction relative to the seat bottom of the seat in which the user sits) but be actuated to move in X- and Y-directions (e.g., within a lateral plane), thereby generally following or mimicking the user's arm movements within a lateral plane. In other words, a powered "floating" arm would generally follow the arm movements of a user (e.g., by sensing directional changes in pressure or pressure distribution with one or more pressure sensors on the arm support linkage that the user's arm is in contact with) while supporting the weight of the user's arm. In some variations, a similar "floating" arm support linkage may be freely movable in X- and Y-directions (e.g., caused by the user's arm pushing and moving the arm support linkage in lateral directions), instead of being movable with actuated, powered joints.

In some variations, the "floating" arm support functionality may be selected as a particular mode, such as with a clutch. For example, when the clutch is disengaged, the arm support linkage may generally be adjustable and lockable in desired configurations as described above. When the clutch is engaged, the arm support linkage may be a "floating" arm support linkage. The clutch may be toggled on and off through, for example, user interaction with the user interface device, foot-operated controls in the user console, voice commands, other external commands, or in any suitable manner.

The arm support linkage may be adjusted in other manners in addition to folded and unfolded configurations. For example, in some variations, the arm support linkage may be adjustable in height (relative to a seat bottom of the seat in which the user sits). In some variations, the height and/or anterior angle of the arm support linkage may correspond to seat configurations that reorient the user position (e.g., seated configuration, reclined configuration, elevated configuration, as described further in U.S. Patent Application No 62/397,823), in order to maintain effective ergonomics. In one variation shown in FIG. 5, an arm support linkage 500' may be coupled to seat 110 through a linkage mount setup 550'. The linkage mount setup 550' includes a slide 552' coupled to the proximal segment 510' (e.g., with fasteners, interlocking features, snap fit, epoxy, etc.) and a slide receptacle 554' coupled to the seat 110 and configured to receive the slide 552'. The slide 552' may be slidingly engaged with the slide receptacle 554' so as to be adjustable in height. For example, the overall height of the arm support linkage 500' relative to the seat 110 may be varied by sliding the slide 552' in and out of the slide receptacle 554'. Height may be adjustable in discrete increments (e.g., using detents) or continuously throughout a range of heights. Adjustment (retraction and extension) of the linkage mount 550' due to the sliding movement of the slide 552' may be adjusted in a manner similar to the adjustment of the arm support linkage described above. For example, the linkage mount 550' may include a brake or clutch that is disengaged and engaged manually and/or electronically. As another example, the connection between the slide 552' and the slide receptacle 554' may be damped (e.g., with a frictional fit, fluid damping mechanism, etc.) to provide substantial resistance against sliding movement away from a particular longitudinal position. As yet another example, the relative sliding movement of the slide 552' and the slide receptacle 554' may be powered by an actuator. Such an actuator may, for example, automatically adjust the height of the arm support linkage according to a user profile or presets, similar to that described above for powered joints in the arm support linkage. For example, a particular height of the arm support linkage may be recalled from a system memory and the slide and/or slide receptacle may be adjusted to correspond to the particular height of the arm support linkage.

Although FIG. 5 illustrates a linkage mount setup 550' in which the slide 552' is coupled to the arm support linkage and the slide receptacle 554' is coupled to the seat 110, it should be understood that in other variations, the various components of the linkage mount setup may be coupled to other portions of the system to facilitate height adjustment of the arm support linkage. For example, as shown in FIG. 6C, a linkage mount setup 650 includes a slide 652 configured to be coupled to a seat 110, and a slide receptacle 654 coupled to the proximal segment 610 and configured to receive the slide 652 in a sliding fashion similar to that described above.

Furthermore, in some variations, configurations and/or heights of multiple arm support linkages in the same user console may be adjustable in a synchronized manner. For example, in variations including two arm support linkages (e.g., a left-side arm support linkage and a right-side arm support linkage), adjustment of one arm support linkage, such as by manual adjustment, may synchronously result in a mirrored adjustment of the other arm support linkage. In one variation, a left-side arm support linkage and a right-side arm support linkage may be coupled to each other or to a common shared adjustable piece, such that their positions are always adjusted together. For example, as shown in FIG. 7A, a right-side arm support linkage 700 and a similar left-side arm support linkage (not shown) may be coupled to the center of the backseat of the seat 110, such as via common shared center mount 710. The center mount 710 may be adjustable along the backseat (e.g., slidingly engaged with a slot or channel on the backseat), thereby mechanically adjusting the height of both the right-side arm support linkage 700 and the left-side arm support linkage at the same time. As another example, as shown in FIG. 7B, a right-side arm support linkage 700 and a left-side arm support linkage 700' may be coupled to a bar 720 located under the seat 110. The bar 720 may be movable closer or farther from the seat 110, thereby mechanically lowering or raising the height of both the right-side arm support linkage 700 and the left-side arm support linkage 700' at the same time. Additionally or alternatively, multiple arm support linkages may be adjustable in a synchronized manner due to simultaneous actuation of powered joints. In some of these variations, multiple arm support linkages may be mechanically separate but synchronously adjustable due to simultaneous actuation of powered joints.

Figure 8:
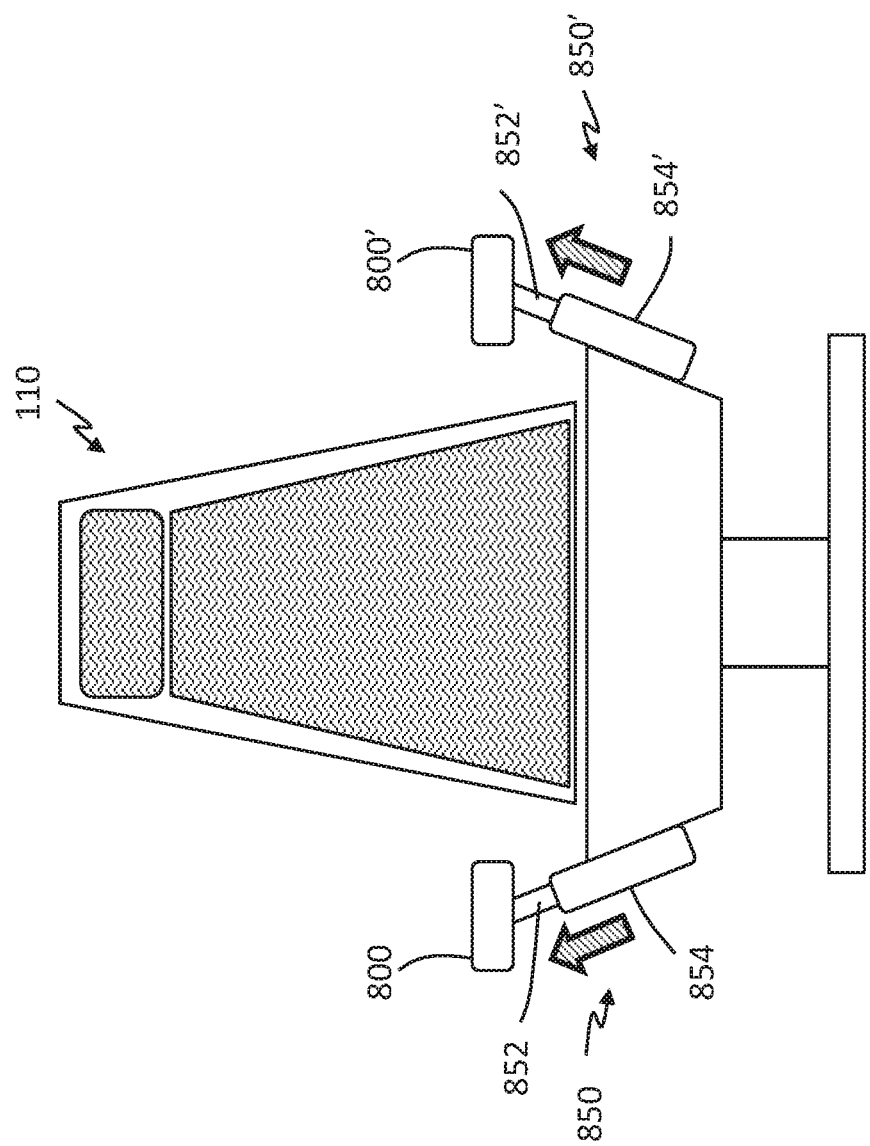
FIG. 8 is a schematic illustration of an exemplary variation of arm support linkages having coupled vertical and lateral angle adjustments.

The lateral angle and/or forward position of the arm support linkage relative to the seat may be adjustable, such as to accommodate a variety of user sizes (e.g., girth of user, arm length of user). In some variations, the adjustment in height, lateral angle, and/or forward position of the arm support linkage may be coupled (e.g., based on a potential assumption that taller users may also have increased girth). For example, as shown in FIG. 8, the arm support linkage 800 may be laterally adjustable with a laterally angled linkage mount setup 850, which includes an angled slide 852 coupled to the arm support linkage 800 and an angled slide receptacle 854 that is coupled to the seat 110. Alternatively, the locations of the angled slide and the angled slide mount may be swapped (e.g., similar to the linkage mount 650 shown in FIG. 6C-6E, except angled laterally outwards to enable synchronous adjustment of both height and lateral angle of the arm support linkage 600). The angled slide 852 may extend and retract within the angled slide receptacle 854 to simultaneously adjust the lateral angle and height of the arm support linkage relative to the seat bottom of the seat S10. The angle of the angled slide 852 and the angled slide mount 854 may be selected to facilitate desired relative rates of lateral angle adjustment and height adjustment. For example, the slide receptacle 854 and slide 852 may be angled anteriorly (upper portions more anterior than lower portions) at an angle between about 5 degrees and about 25 degrees, between about 10 degrees and 20 degrees, or about 15 degrees, while they may be angled laterally (upper portions more lateral than lower portions) at an angle between about 5 degrees and about 15 degrees, or about 10 degrees. Alternatively, in some variations, the angled slide 852 may be coupled to the seat 110 via a pivot joint that is configured to selectively rotate laterally outward and inward, independent of adjustment of arm support linkage height. Such a pivot joint may include a brake and/or be controlled manually or with an actuator as a powered joint. As another example, the general forward position and height of the arm support linkage 800 may be adjusted substantially simultaneously (e.g., if the angled slide receptacle 854 and angled slide 852 are angled anteriorly, such that as the angled slide 852 extends and retracts within the angled slide 854, the position of the arm support linkage 800 is moved anteriorly and posteriorly, respectively. For example, the slide receptacle 854 and slide 852 may be angled anteriorly (upper portions more anterior than lower portions) at an angle between about 20 degrees and about 40 degrees, or about 30 degrees.

In some variations, at least a portion of the arm support linkage may include cushioning to increase user comfort. For example, foam, silicone gel, or other suitable padding may be located on an upper surface of the arm support linkage configured to be in contact with a user's arm. Additionally or alternatively, an upper surface of the arm support linkage may be contoured (e.g., with a convex surface) to more comfortably receive a user's arm. The cushioning and/or contouring may be strategically placed to encourage the user to rest his or her arms on a particular desired portion of the arm support linkage, thereby encouraging a more ergonomic posture and use of the user console when the user is maneuvering the user interface device. For example, when performing at least some surgical tasks, it may be more ergonomic for a user to keep the user's arms relatively tucked in at the user's sides, instead of allowing the user's arms to move extensively laterally outwards. Accordingly, referring to FIG. 3B, the distal segment 330 may include cushioning and/or contouring, while the proximal segment 310 and/or the intermediate segment 320 may lack cushioning and/or contouring. The selective placement of cushioning and/or contouring on only the distal segment 330 may be a subtle encouragement for the user to rest his or her arms on only the distal segment 330 when the arm support linkage is in an unfolded use configuration.

Figure 9:
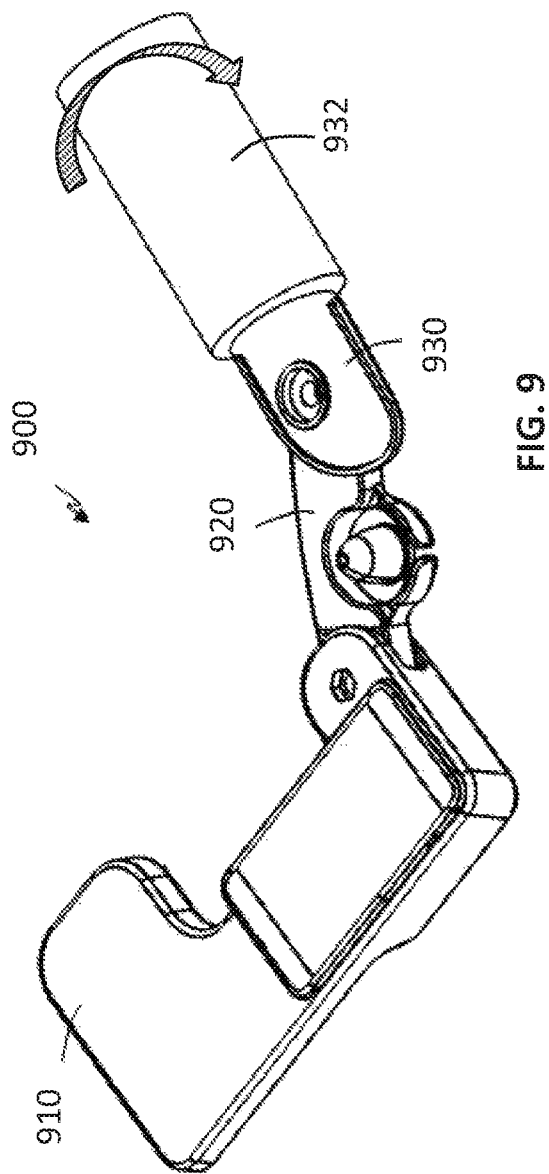
FIG. 9 is a schematic illustration of an exemplary variation of an arm support linkage having a rotatable cushion.

Other variations of arm support linkages may include rolling or rotatable cushions to further support a user's arms during forward and rearward arm movements (e.g., when maneuvering the user interface devices with a forward and rearward movement to command movement of an instrument longitudinally along its instrument shaft). For example, as shown in FIG. 9, an arm support linkage 900 may include proximal, intermediate, and distal segments 910, 920, and 930, respectively, which may be similar to those in arm support linkage 300 described above with reference to FIGS. 4A-4E, except for the addition of a generally cylindrical cushion 932 disposed around the surface of the distal segment 930 and configured to rotate around a longitudinal axis of the distal segment 930. The cushion 932 may be mounted, for example, on a radial bearing coupled to the distal segment 930. As such, the user's arm may be supported by the cushioned distal segment 930 when the arm support linkage is in an unfolded configuration, and may continue to be supported throughout a user's forward and/or rearward arm movements as the cushion 932 rolls with the user's arm. In other words, in order to move his arms forward or backward, the user need not lift his arms off of the arm support linkage, and may be fully supported in an ergonomic fashion throughout a variety of arm movements. In some variations, a similar effect may be accomplished by including a roll joint in the arm support linkage. For example, with reference to FIG. 4D, the distal segment 330 may be configured to roll relative to the intermediate segment 320, such as via a roll joint located adjacent to pin joint 322.

Sensors

Figure 10:
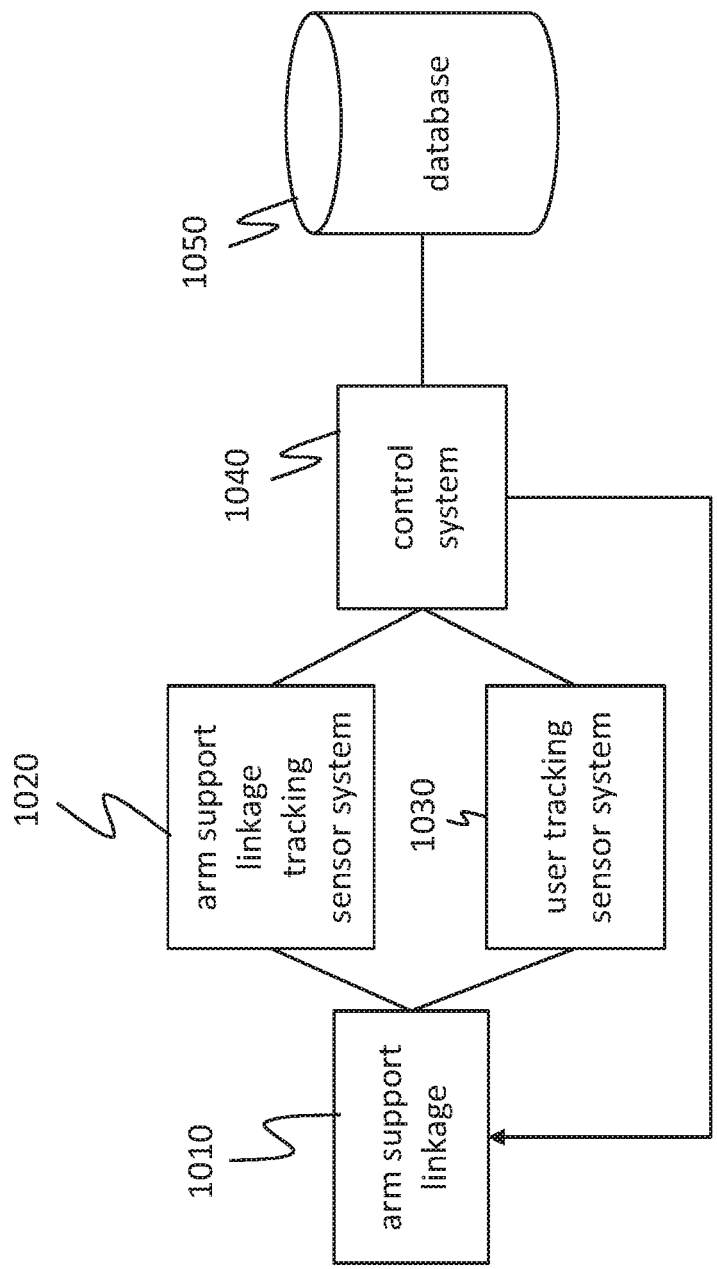
FIG. 10 is a schematic illustration of a control system with sensor systems for improving usage of the arm support linkage by a user.

In some variations, the arm support linkage and/or other portions of the user console may include one or more various sensor systems for tracking status information of the arm support linkage and its use. For example, as shown in FIG. 10, the system may include an arm support linkage tracking sensor system 1020 and/or a user tracking sensor system 1030. The arm support linkage tracking sensor system 1020 may be configured to detect a configuration (e.g., position) or other status of at least a portion of the arm support linkage 1010. The user tracking sensor system 1030 may be configured to detect a user arm position relative to the arm support linkage 1010 (e.g., contact between the user arm and the arm support linkage, distance between the user arm and the arm support linkage, etc.). Information from the sensors may be used, for example, to generate data regarding optimum positioning of one or more arm support linkages for a variety of users performing a variety of surgical tasks. This data may be stored and/or retrieved from a database 1050 providing information regarding ergonomic positioning of the arm support linkage 1010 for different users, different surgical tasks, etc. Furthermore, as another example, information from the sensors may be used to characterize usage of the one or more arm support linkages by the user controlling the robotic surgical system from the user console. A control system 1040 may be in communication with the database 1050 and the arm support linkages to improve or correct the usage of the one or more arm support linkages by the user (e.g., for ergonomic or efficiency purposes).

The arm support linkage tracking sensor system 1020 may, in some variations, include at least one position sensor configured to detect and/or characterize a position of at least a portion of the arm support linkage. For example, the arm support linkage may include at least one rotary encoder for measuring rotational position of joints in the arm support linkage. The current configuration of the arm support linkage may be determined based on knowledge of the rotational position of each joint (as measured by an encoder or otherwise known) in the arm support linkage. As another example, at least one marker (e.g., infrared marker) may be coupled to one or more portions of the arm support linkage to facilitate optical tracking of the positions of the arm support linkage via one or more overhead or surrounding tracking sensors to detect the position of the arm support linkage. As another example, one or mom proximity sensors on different portions of an arm support linkage (and/or on different arm support linkages in a user console) may detect relative positions of different portions of an arm support linkage (e.g., distance between a proximal portion and a distal portion of an arm support linkage) and/or relative positions of different arm support linkages (e.g., distance between a left-side arm support linkage and a right-side arm support linkage). As yet another example, one or more proximity sensors or other suitable sensor on an arm support linkage and/or at least one user interface device may enable detection of relative positions of the arm support linkage and the at least one user interface device (e.g., to characterize how the user is holding the user interface device relative to the arm support linkage, to detect docking or undocking of the user interface device in the arm support linkage or other docking location, etc.). Other suitable sensors configured for detecting position of the arm support linkage may additionally or alternatively be included in the tracking sensor system 1020.

The user tracking sensor system 1030 may include one or more sensors configured to indicate and/or characterize contact of the user's arm with the one or more arm support linkages, or the relative position of the user's arm with the one or more arm support linkages. For example, the arm support linkage (e.g., a cushioned surface or other surface configured to receive contact with the user's arm) may include one or more capacitive sensors configured to detect contact between the user and the arm support linkage. As another example, the arm support linkage may include one or more pressure transducers or other sensors configured to detect distribution of pressure on the arm support linkage caused by the user's arm. As yet another example, the arm support linkage may include a proximity sensor (e.g., capacitive, inductive, optical, etc.) configured to measure the distance between the user's arm and the arm support linkage. In some variations, the user may don accessories (e.g., optical markers, gloves, arm bands, etc.) to help facilitate tracking of the user's arm relative to the arm support linkage.

The database 1050 may include any suitable local or remote storage device, such as a hard drive, flash memory, server system, etc. The control system 1040 may be in communication with the database 1050 and/or arm support linkage 1010 (and/or other portions of the user console) with a wireless or wired connection. The control system 1040 may be implemented on one or more processors configured to execute instructions stored in memory such that, when it executes the instructions, the processor performs aspects of the methods described herein. The instructions may be stored on memory or other computer-readable medium such as RAMs, ROMs, flash memory, EEPROMs, optical devices (e.g., CD or DVD), hard drives, floppy drives, or any suitable device.

The information provided by the arm support linkage tracking sensor system 1020 and/or the user tracking sensor system 1030 may be used to characterize a variety of aspects of how a user is using the arm support linkage. In one variation, determination of the position of the arm support linkage and knowledge of contact between the user's arm and the arm support linkage may characterize where the user's arm is in relation to the trackable workspace of the user interface device. For example, the system may provide feedback (e.g., haptic feedback, such a vibrational alert with a vibrational motor in the handheld user interface device) when the user's arm is characterized as nearing a boundary of the trackable workspace of the user interface device.

As another variation, position of the arm support linkage may be characterized and recorded for individual users. For example, a particular position of the arm support linkage (e.g., a preferred configuration that the user indicates is ergonomic and comfortable) may be detected and stored in a database. The preferred configuration may be associated in the database with a particular user profile, such that in a subsequent surgical operating session, a user may be able to retrieve his or her preferred configuration and have the arm support linkage be quickly adjusted (e.g., automatically via powered joints) to the preferred configuration. For example, as described elsewhere herein, a preferred configuration may be recalled from a system memory and the arm support linkage may be actuated to effect the preferred configuration (e.g., a particular unfolded configuration, height, etc.) of the arm support linkage, such as by a predetermined trajectory of one or more joints simultaneously or sequentially.

The position of the arm support linkage may be used as an interlock for teleoperation of the robotic surgical system. For example, the user interface device may be disabled and prevented from controlling the robotic surgical system, if the tracking sensor system 1020 detects that the arm support linkage is in a folded configuration (which suggests that a user is not secured in the seat). Once the tracking sensor system 1020 detects that the arm support linkage is in a suitable unfolded configuration (which suggests that a user is secured in the seat), the user interface device may be operational for teleoperation of the robotic surgical system. Furthermore, contact, pressure, and/or proximity sensors may be additionally or alternatively used as a similar interlock. For example, the user interface device may be disabled (and/or certain controls, such as tasks generally requiring fine movement control) if the user tracking sensor system 1030 detects that the user's arm is not in contact with and/or is lifted too high away from the arm support linkage. The user interface device may be enabled once the user tracking sensor system 1030 detects that the user's arm is in sufficient contact with and resting on the arm support linkage.

In another variation, at least one of the tracking sensor systems may receive other forms of user input for controlling the robotic surgical system and/or user console. For example, if a user exerts pressure on the arm support linkage (e.g., downward or in another angular direction, which may be detected by pressure sensors, etc.) that exceeds a predetermined threshold, then the system may automatically adjust the height and/or angle of the arm support linkage and/or activate an adjustment setting enabling the user to manually adjust the height and/or angle of the arm support linkage. As another example, similarly, if a user exerts pressure on the arm support linkage in a particular spatial and/or temporal manner (e.g., double-tapping on the top of the arm support linkage or tapping the top of the arm support linkage in a particular location(s) on the arm support linkage, etc.), then the system may automatically adjust the height and/or angle of the arm support linkage, and/or activate an adjustment setting such as that described above.

In another variation, the user tracking sensor system 1030 may provide metrics regarding efficiency of one's use of the arm support linkage. For example, contact or pressure sensors may detect how often the user is touching the arm support linkage and/or how often the user is lifting his arm off of the arm support linkage (generally, the more often the user's arm is in contact with the arm support linkage, the more efficient the user's use of the arm support linkage). Such metrics may, for example, be useful for providing feedback to a user undergoing training in a user console and learning how to operate the user system for the robotic surgical system in an efficient manner with minimal fatigue, etc. For example, positional data of the arm support linkage (e.g., absolute position, position relative to the user and/or user interface devices, etc., which may be detected as described above) may be useful for generating suggestions or recommendations to the user for height, angle, configuration, etc. of the arm support linkage. As an illustrative example, the positional data and/or contact use data for the arm support linkage may be interpreted to determine that the user is primarily working above or below an ideal arm support linkage height, and accordingly the system may provide an alert to the user recommending that a height adjustment is made for better ergonomics, better control of the robotic surgical system, etc. Alternatively, the system may automatically adjust the height of the arm support linkage to the ideal height. Furthermore, in some variations, the sensors may be used to generate a database of how the system is utilized by users of different kinds and for different kinds of surgical tasks. The database 1050 may be used to help develop suggested positioning for ergonomic and efficient use of the arm support linkage, such as for use during a surgical procedure and/or for providing feedback during training in preparation for the user performing surgical procedures. For example, for each of a plurality of users using the arm support linkage and for various different surgical tasks, the position of the arm support linkage may be recorded and stored in the database. Furthermore, contact or pressure sensors may provide metrics on the user's efficiency of use of the arm support linkage, as described above. Accordingly, the database may store arm support linkage positions that are most frequently used and/or are associated with the most efficient use of the arm support linkage. In some variations, the tracking sensor systems 1020 and 1030 may be combined with positional data from the user interface device(s) and transmitter(s), along with additional sensors in the user console, to indicate ergonomic use, and proprioception (eye to arm positioning), etc. The stored configurations of the arm support linkage may be stored in the database associated with a user characteristic (e.g., user height, weight, girth, etc.) and/or a surgical task characteristic (e.g., surgical procedure or type of arm movements involved).

Figure 11:
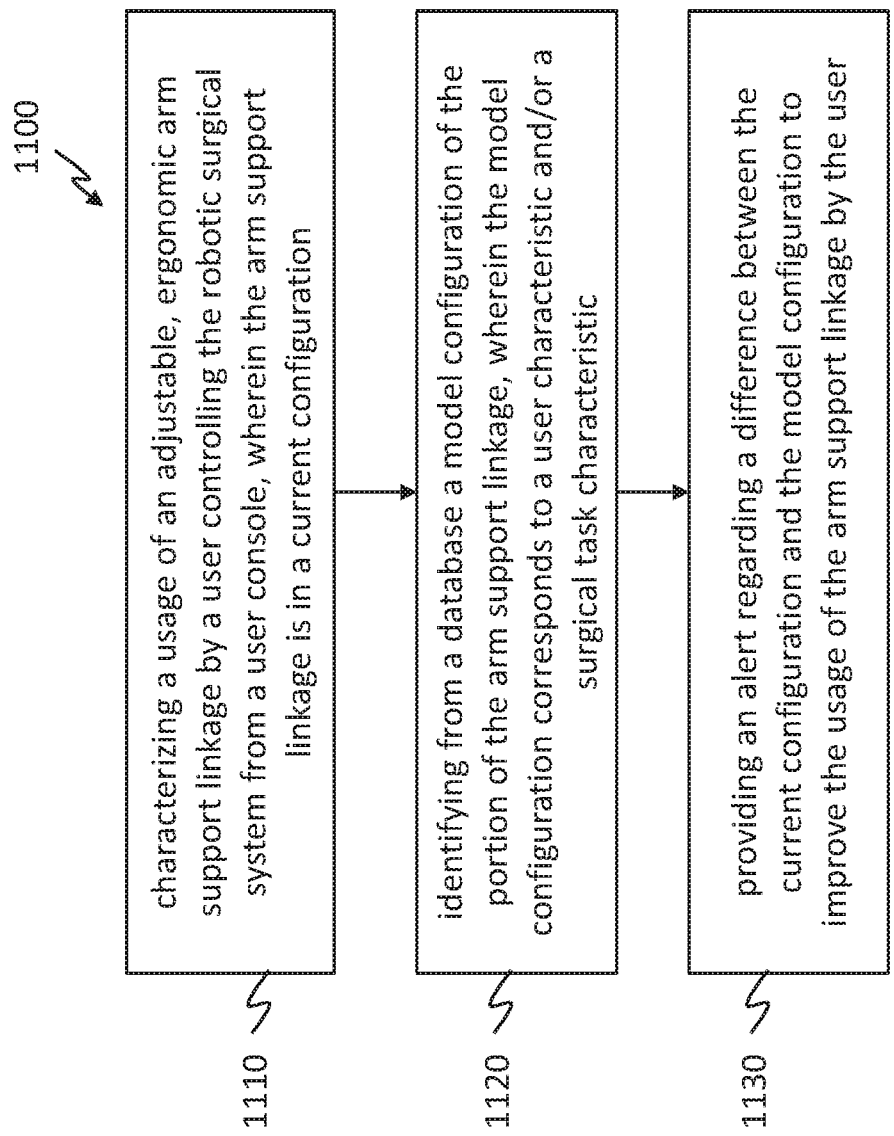
FIG. 11 is an exemplary flowchart depicting a method for operating a user system for a robotic surgical system.

After collecting data, the tracking sensor systems 1020 and 1030 may provide input into the control system 1040 to provide feedback to the user and/or the system, or suggestions to improve the usage of the arm support linkage (e.g., for improvements in ergonomics and/or efficiency). For example, as shown in FIG. 11, generally in some variations, a method 1100 for operating a user system for a robotic surgical system includes characterizing a usage of an adjustable ergonomic arm support linkage 1110 by a user controlling the robotic surgical system from a user console, where the arm support linkage is in a current configuration. The method may further include identifying, from a database, a model configuration of the portion of the arm support linkage 1120, where the model configuration corresponds to a user characteristic and/or a surgical task characteristic. As described above, the model configuration may be a stored preset configuration that is a likely candidate (e.g., as determined through empirical data such as previous users' stored configurations) for improved ergonomic and/or efficient use of the arm support linkage.

After identifying a suggested model configuration, the method 1100 may include providing an alert regarding a difference between the current configuration and the model configuration 1130 to improve the usage of the arm support linkage by the user. The alert may include, for example, a visual alert (e.g., displayed on an open display or the display on the arm support linkage), or an audio alert on speakers, to notify that correction in the position of the arm support linkage may be advisable.

Additionally or alternatively, the method 1100 may include actuating one or more joints in the arm support linkage to assume the model configuration based on the difference between the current configuration and the model configuration. For example, the method may including moving the arm support linkage to assume the model configuration to generally provide a corrected, optimal kind of arm support to the user for that user's type and/or the task being performed by the user. Accordingly, the user may be provided with position feedback for ergonomic and efficient use of the arm support linkage when the control system recalls the appropriate model configuration from the database and implements it in the arm support linkage if the current configuration deviates enough from the model configuration.

Other Electronics

In some variations, the arm support linkage may include at least one display. The display may, for example, be a touch screen device configured to receive user input such as for user login and/or selection of presets (e.g., user console seat configurations, arm support linkage configurations, etc.). For example, the display may be used to receive user input for recalling stored configurations (e.g., stored unfolded configurations, heights, etc.) of the arm support linkage. Such user input may, for example, include passcode, user identification code, fingerprint, etc. through the display, or additionally or alternatively other user identification processes such as voice or facial recognition. The display may additionally or alternatively be configured to display information of interest to the user (e.g., medical image data, status of the robotic surgical system, etc.) from a location that is easily viewable by the user. The display may be removable from or permanently affixed to the arm support linkage (or other portion of the seat of the user console). In some variations, the display may include features similar to that of the auxiliary display described in U.S. Patent Application No. 62/397,823.

In some variations, as shown in FIGS. 4A-4E, a display 340 may be mounted on the proximal segment 310. In view of other features (e.g., cushioning on the distal segment 330 only) that may encourage the user to primarily rest his arms on the distal segment 330, the arrangement of the display 340 on the proximal segment 310 may substantially protect the display 340 from damage by the user's arm. The display 340 may be inset in the proximal segment 310 (e.g., with a bezel) for further protection. In some variations, the display 340 may be removable and replaceable (e.g., with a snap fit).

Additionally or alternatively, the display may be coupled to a display mount that may elevate the display above or away from the arm support linkage. For example, as shown in FIG. 5, a display 540 may be coupled to the arm support linkage 500 with a mount arm 542. The mount arm 542 may be adjustable in length and/or angle to facilitate positional adjustment of the display 540. Furthermore, in some variations, the mount arm 542 may be foldable or include telescoping segments, such that the display 540 and/or mount arm 542 may be compacted against the arm support linkage or other portion of the user console (e.g., when the arm support linkage 500 is in its folded configuration).

In some variations, the arm support linkage (or other suitable portion of the user console) may include at least one transmitter configured to communicate with the user interface device(s). For example, the transmitter may be configured to receive command signals from the user interface device (e.g., magnetic tracking of position of the user interface device as the user manipulates it) and transmit the command signals to a control system for interpretation and control of the robotic surgical system based on the transmitted signals. By locating the transmitter in the arm support linkage and near the user interface device(s) when they are in use, the arrangement may increase signal precision (by reducing noise, interference, and/or other effects that magnified by increased distance between the user interface device(s) and the transmitter). Furthermore, the arrangement may advantageously allow a lower strength of magnetic field that is required for magnetic tracking of the user interface device.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A method for operating a user console for a robotic surgical system, the method comprising:
   characterizing a usage of at least a portion of an adjustable, ergonomic arm support linkage by a user controlling the robotic surgical system from a user console, wherein the portion of the arm support linkage is in a current configuration;
   identifying from a database a model configuration of the portion of the arm support linkage, wherein the model configuration corresponds to at least one of a user characteristic and a surgical task characteristic; and
   providing an alert regarding a difference between the current configuration and the model configuration of the portion of the arm support linkage to improve the usage of the arm support linkage by the user.

2. The method of claim 1, wherein characterizing the usage comprises detecting at least one of a position and orientation of the portion of the arm support linkage with a tracking sensor system.

3. The method of claim 1, further comprising storing in memory the characterization of the usage and associating the stored characterization with at least one of a user characteristic and a surgical task characteristic.

4. The method of claim 1, further comprising actuating one or more joints in the arm support linkage to assume the model configuration based on the difference between the current configuration and the model configuration.

5. The method of claim 1, further comprising detecting a user arm position relative to the arm support linkage with a user tracking sensor system.

6. The method of claim 5, wherein detecting a user arm position comprises detecting contact between the user arm position and the arm support linkage.

7. The method of claim 5, further comprising actuating one or more joints in the arm support linkage to follow the detected user arm position in a clutch engagement mode.

8. The method of claim 1, further comprising disabling a user interface device for controlling the robotic system, in response to detecting a folded configuration of the portion of the arm support linkage.

9. The method of claim 1, wherein the alert comprises a visual alert displayed on an open display or a display on the arm support linkage notifying that a correction in a position of the portion of the arm support linkage is advisable.

10. The method of claim 1, wherein the alert comprises an audio alert notifying that a correction in a position of the portion of the arm support linkage is advisable.

* * * * *